(12) United States Patent
Bode

(10) Patent No.: US 9,675,649 B2
(45) Date of Patent: Jun. 13, 2017

(54) DISIALYLLACTO-N-TETRAOSE (DSLNT) OR VARIANTS, ISOMERS, ANALOGS AND DERIVATIVES THEREOF TO PREVENT OR INHIBIT BOWEL DISEASE

(75) Inventor: Lars Bode, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/983,624

(22) PCT Filed: Feb. 3, 2012

(86) PCT No.: PCT/US2012/023866
§ 371 (c)(1),
(2), (4) Date: Aug. 5, 2013

(87) PCT Pub. No.: WO2012/106665
PCT Pub. Date: Aug. 9, 2012

(65) Prior Publication Data
US 2013/0315990 A1    Nov. 28, 2013

Related U.S. Application Data

(60) Provisional application No. 61/439,705, filed on Feb. 4, 2011.

(51) Int. Cl.
| | | |
|---|---|---|
| *A61K 31/702* | (2006.01) | |
| *A61K 35/74* | (2015.01) | |
| *A61K 35/742* | (2015.01) | |
| *A61K 35/741* | (2015.01) | |
| *G01N 33/50* | (2006.01) | |
| *A23K 40/10* | (2016.01) | |
| *A23K 10/18* | (2016.01) | |
| *A23K 20/163* | (2016.01) | |
| *A23K 50/00* | (2016.01) | |
| *A23P 10/28* | (2016.01) | |
| *A23L 29/30* | (2016.01) | |
| *A23L 33/00* | (2016.01) | |
| *A23L 33/135* | (2016.01) | |

(52) U.S. Cl.
CPC ............ *A61K 35/742* (2013.01); *A23K 10/18* (2016.05); *A23K 20/163* (2016.05); *A23K 40/10* (2016.05); *A23K 50/00* (2016.05); *A23L 29/30* (2016.08); *A23L 33/135* (2016.08); *A23L 33/40* (2016.08); *A23P 10/28* (2016.08); *A61K 31/702* (2013.01); *A61K 35/741* (2013.01); *G01N 33/50* (2013.01); *G01N 2400/00* (2013.01); *G01N 2800/065* (2013.01); *G01N 2800/067* (2013.01); *G01N 2800/38* (2013.01); *G01N 2800/7095* (2013.01)

(58) Field of Classification Search
None
See application file for complete search history.

(56) References Cited

U.S. PATENT DOCUMENTS

| 6,576,251 | B1 | 6/2003 | Stahl et al. | |
|---|---|---|---|---|
| 2005/0070464 | A1* | 3/2005 | Stahl et al. | 514/8 |
| 2007/0275881 | A1* | 11/2007 | Morrow et al. | 514/8 |
| 2009/0197806 | A1 | 8/2009 | Morrow et al. | |
| 2010/0278781 | A1 | 11/2010 | Hougee et al. | |

FOREIGN PATENT DOCUMENTS

| CA | 2 636 724 | 8/2007 |
|---|---|---|
| CA | 2 767 043 | 1/2011 |
| EP | 1974735 | * 3/2007 |
| EP | 12742191 | 7/2015 |
| WO | WO 2005/055944 | 6/2005 |

OTHER PUBLICATIONS

Lara-Villoslada, F. et al "Beneficial effects of probiotic bacteria . . . " Br. J. Nutr. (2007) vol. 98, Suppl. 1, pp. S96-S100.*
Stehle, T. et al "High-resolution structure of polyomavirus VP1-oligosaccharide complex . . . " The EMBO J. (1987) vol. 16, No. 16, pp. 5139-5148.*
Dey, N. et al "Multiparticulated drug delivery systems . . . " Trop. J. Pharm. Res. (2008) vol. 7, No. 3, pp. 1067-1075.*
Komagome, R. et al "Oligosaccharides as receptors for JC virus" J. Virol. (2002) vol. 76, No. 24, pp. 12992-13000.*
Pikulski, M. et al "Sequencing and characterization of oligosaccharides . . . " J. Am. Soc. Mass Spectrom. (2007) vol. 18, pp. 2094-2106.*
Grimmonprez, L. et al "Determination de la structure d'un hexaose . . . " Eur. J. Biochem. (1970) vol. 13, pp. 484-492.*
Glycoseparations catalogue excerpt for "Sialated oligosaccharides from human milk and urine" (undated) Retrieved from the Internet Feb. 26, 2015. URL: http://www.glycoseparations.com/catalogue/catalogue.pdf.*
Grimmonprez, L. et al "Etude physico-chimique de six nouveaux oligosides . . . " Bull. Soc. Chim. Biol. (1968) vol. 50, No. 4, pp. 843-855.*
Stahl, B. et al "Oligosaccharides from human milk as revealed . . . " Anal. Biochem. (1994) vol. 223, pp. 218-226.*
Difilippo, E. et al "Comparison of milk oligosaccharides pattern . . . " J. Agric. Food Chem. (2015) vol. 63, pp. 4805-4814.*
Enzo catalog entry for ganglioside GD1a entry. http://www.enzolifesciences.com/ALX-302-007/ganglioside-gd1a-.-disodium-salt-bovine-brain/ Retrieved online May 2, 2016.*
Updegrove, K. "Necrotizing enterocolitis: the evidence for . . . " J. Hum. Lact. (2004) vol. 20, No. 3, pp. 335-338.*
Bao, Yuanwu et al., "Simultaneous quantification of sialyloligosaccharides from human milk by capillary electrophoresis," *Anal Biochem*, 2007, 370:206-14 (Exhibit 4).
Becker, Daniel J. and John B. Lowe, "Leukocyte adhesion deficiency type II," *Biochimica et Biophysica Acta*, 1999, 1455:193-204 (Exhibit 5).

(Continued)

*Primary Examiner* — Leigh C Maier
(74) *Attorney, Agent, or Firm* — Gavrilovich, Dodd & Lindsey LLP

(57) ABSTRACT

The invention provides formulations comprising isolated Disialyllacto-N-tetraose (DSLNT) or variants, isomers, analogs and derivatives thereof.

5 Claims, 20 Drawing Sheets

(56) References Cited

OTHER PUBLICATIONS

Blakely, Martin L. et al., "Postoperative Outcomes of Extremely Low Birth-Weight Infants With Necrotizing Enterocolitis or Isolated Intestinal Perforation: A Prospective Cohort Study by the NICHD Neonatal Research Network," *Annals of Surgery*, 2005, 241:984-94 (Exhibit 6).

Blank, Dennis et al., "High-throughput mass finger printing and Lewis blood group assignment of human milk oligosaccharides," *Anal Bioanal Chem*, 2011, 401:2495-510 (Exhibit 7).

Bode, Lars, "Recent Advances on Structure, Metabolism, and Function of Human Milk Oligosaccharides," *The Journal of Nutrition*, 2006, 136:2127-30 (Exhibit 8).

Bode, Lars, "Human milk oligosaccharides: prebiotics and beyond," *Nutrition Reviews*, 2009, 67:S183-91 (Exhibit 9).

Bode, Lars et al., "Human milk oligosaccharides reduce platelet-neutrophil complex formation leading to a decrease in neutrophil β 2 integrin expression," *Journal of Leukocyte Biology*, 2004, 76:820-6 (Exhibit 10).

Bode, Lars et al., "Inhibition of monocyte, lymphocyte, and neutrophil adhesion to endothelial cells by human milk oligosaccharides," *Thromb Haemost*, 2004, 92:1402-10 (Exhibit 11).

Clark, R. H. et al., "Characteristics of patients who die of necrotizing enterocolitis," *Journal of Perinatology*, 2012, 32:199-204 (Exhibit 12).

Crocker, Paul R. et al., "Siglecs and their roles in the immune system," *Nature Reviews*, 2007, 7:255-66 (Exhibit 13).

Dicken, Bryan J. et al., "Medical management of motility disorders in patients with intestinal failure: a focus on necrotizing enterocolitis, gastroschisis, and intestinal atresia," *Journal of Pediatric Surgery*, 2011, 46:1618-30 (Exhibit 14).

Ganapathy, Vaidyanathan et al., "Costs of Necrotizing Enterocolitis and Cost-Effectiveness of Exclusively Human Milk-Based Products in Feeding Extremely Premature Infants," *Breastfeeding Medicine*, 2012, 7:29-37 (Exhibit 15).

Guner, Yigit S. et al., "P-glycoprotein induction by breast milk attenuates intestinal inflammation in experimental necrotizing enterocolitis," *Laboratory Investigation*, 2011, 91:1668-79 (Exhibit 16).

Holman, Robert C. et al., "The Epidemiology of Necrotizing Enterocolitis Infant Mortality in the United States," *American Journal of Public Health*, 1997, 87:2026-31 (Exhibit 17).

Holman, Robert C. et al., "Necrotising enterocolitis hospitalisations among neonates in the United States," *Paedriatic and Perinatal Epidemiology*, 2006, 20:498-506 (Exhibit 18).

Jantscher-Krenn, Evelyn et al., "The human milk oligosaccharide disialyllacto-N-tetraose prevents necrotizing enterocolitis in neonatal rats," *Gut*, 2011, pp. 1-9 (Exhibit 19).

Kobata, Akira, "Structures and application of oligosaccharides in human milk," *Proc. Jpn. Acad. Ser. B*, 2010, 86:731-47 (Exhibit 20).

Koliwer-Brandl, Hendrik et al., "Lectin inhibition assays for the analysis of bioactive milk sialoglycoconjugates," *International Dairy Journal*, 2011, 21:413-20 (Exhibit 21).

Kunz, C. and S. Rudloff, "Potential Anti-Inflammatory and Anti-Infectious Effects of Human Milk Oligosaccharides," *Advances in Experimental Medicine and Biology*, 2008, 606:455-65 (Exhibit 22).

Kunz, C. et al., "Oligosaccharides in Human Milk: Structural, Functional, and Metabolic Aspects," *Annu. Rev. Nutr.*, 2000, 20:699-722 (Exhibit 23).

Kuntz, Sabine et al., "Oligosaccharides from human milk influence growth-related characteristics of intestinally transformed and non-transformed intestinal cells," *British Journal of Nutrition*, 2008, 99:462-71 (Exhibit 24).

Leo, Fiame et al., "Determination of Sialyl and Neutral Oligosaccharide Levels in Transition and Mature Milks of Samoan Women, Using Anthranilic Derivatization Followed by Reverse Phase High Performance Liquid Chromatography," *Biosci. Biotechnol. Biochem.*, 2010, 74:298-303 (Exhibit 25).

Lucas, A. and T. J. Cole, "Breast milk and neonatal necrotising enterocolitis," *Lancet*, 1990, 336:1519-23 (Exhibit 26).

Lühn, Kerstin et al., "The gene defective in leukocyte adhesion deficiency II encodes a putative GDP-fucose transporter," *Nature Genetics*, 2001, 28:69-72 (Exhibit 27).

Nadler, Evan P. et al., "Expression of Inducible Nitric Oxide Synthase and Interleukin-12 in Experimental Necrotizing Enterocolitis," *Journal of Surgical Research*, 2000, 92:71-7 (Exhibit 28).

Neu, Josef and W. Allan Walker, "Necrotizing Enterocolitis," *The New England Journal of Medicine*, 2011, 364:255-64 (Exhibit 29).

Newburg, David S. et al., "Human Milk Glycans Protect Infants Against Enteric Pathogens," *Annu. Rev. Nutr.*, 2005, 25:37-58 (Exhibit 30).

Rees, Clare M. et al., "Neurodevelopmental outcomes of neonates with medically and surgically treated necrotizing enterocolitis," *Arch Dis Child Fetal Neonatal Ed*, 2007, 92:F193-8 (Exhibit 31).

Schanler, Richard J. et al., "Feeding Strategies for Premature Infants: Beneficial Outcomes of Feeding Fortified Human Milk Versus Preterm Formula," *Pediatrics*, 1999, 103:1150-7 (Exhibit 32).

Schanler, Richard J. et al., "Randomized Trial of Donor Human Milk Versus Preterm Formula as Substitutes for Mothers' Own Milk in the Feeding of Extremely Premature Infants," *Pediatrics*, 2005, 116:400-6 (Exhibit 33).

Sisk, P. M. et al., "Early human milk feeding is associated with a lower risk of necrotizing enterocolitis in very low birth weight infants," *Journal of Perinatology*, 2007, 27:428-33 (Exhibit 34).

Sodhi, Chhinder et al., "The development of animal models for the study of necrotizing enterocolitis," *Disease Models & Mechanisms*, 2008, 1:94-8 (Exhibit 35).

Stahl, Bernd et al., "Oligosaccharides from Human Milk as Revealed by Matrix-Assisted Laser Desorption/Ionization Mass Spectrometry," *Analytical Biochemistry*, 1994, 223:218-26 (Exhibit 36).

Stefanutti, Giorgio et al., "P-selectin expression, neutrophil infiltration, and histologic injury in neonates with necrotizing enterocolitis," *Journal of Pediatric Surgery*, 2005, 40:942-8 (Exhibit 37).

Sullivan, Sandra et al., "An Exclusively Human Milk-Based Diet Is Associated with a Lower Rate of Necrotizing Enterocolitis than a Diet of Human Milk and Bovine Milk-Based Products," *The Journal of Pediatrics*, 2010, 156:562-7 (Exhibit 38).

Thurl, Stephan et al., "Detection of four human milk groups with respect to Lewis blood group dependent oligosaccharides," *Glycoconjugate Journal*, 1997, 14:795-9 (Exhibit 39).

Tickell, David and Trevor Duke, "Evidence behind the WHO guidelines: Hospital Care for Children: For Young Infants with Suspected Necrotizing Enterocolitis (NEC), What is the Effectiveness of Different Parenteral Antibiotic Regimens in Preventing Progression and Sequelae?," *Journal of Tropical Pediatrics*, 2010, 56:373-8 (Exhibit 40).

Uauy, Ricardo D. et al., "Necrotizing enterocolitis in very low birth weight infants: Biodemographic and clinical correlates," *The Journal of Pediatrics*, 1991, 119:630-8 (Exhibit 41).

Upperman, Jeffrey S. et al., "Mechanisms of nitric oxide-mediated intestinal barrier failure in necrotizing enterocolitis," *Seminars in Pediatric Surgery*, 2005, 14:159-66 (Exhibit 42).

Wu, Shuai et al., "The development of an annotated library of neutral human milk oligosaccharides," *J Proteome Res*, 2010, 9:4138-51 (Exhibit 43).

Wu, Shuai et al., "Annotation and Structural Analysis of Sialylated Human Milk Oligosaccharides," *J Proteome Res*, 2011, 10:856-68 (Exhibit 44).

Young, Christopher et al., "Biomarkers for Infants at Risk for Necrotizing Enterocolitis: Clues to Prevention?," *Pedriatr Res*, 2009, 65:91R-7R (Exhibit 45).

\* cited by examiner

B    DF    FF    FF+HMO

FIGURE 6-2

DISIALYLLACTO-N-TETRAOSE (DSLNT) OR VARIANTS, ISOMERS, ANALOGS AND DERIVATIVES THEREOF TO PREVENT OR INHIBIT BOWEL DISEASE

This application is a 371 application of PCT application No. PCT/US2012/023866, filed Feb. 3, 2012, which claims the priority of U.S. Ser. No. 61/439,705, filed Feb. 4, 2011, the contents of all of which are hereby incorporated by reference in their entirety into the present application.

This invention was made with government support under Grant No. K99/R00 DK078668 awarded by NIH/NIDDK. The government has certain rights in the invention.

Throughout this application various publications are referenced. The disclosures of these publications in their entirety are hereby incorporated by reference into this application in order to more fully describe the state of the art to which this invention pertains.

BACKGROUND OF THE INVENTION

Necrotizing Enterocolitis (NEC) is one of the most frequent and fatal intestinal disorders in preterm infants. Almost 10% of very-low-birth-weight infants (<1,500 g birth weight) develop NEC. More than 25% of them die from the disorder. The survivors are often faced with long-term neurological impairment. In 1990, Lucas and Cole (Lancet, 336:1519-23) had already reported that formula-fed infants are at a 6- to 10-fold higher risk to develop NEC when compared to breast-fed infants. Since then several molecules in human milk (e.g. LC-PUFA, PAF-AH, EGF) have been associated with NEC protection, mostly based on animal studies. However, despite improvements in formula composition over the past 10-15 years, formula-fed infants are still at a 6- to 10-fold higher risk than breast-fed infants. The data suggests that human milk contains something else that is missing in formula and protects breast-fed infants from NEC. Identifying the protective component in human milk as well as its mechanisms of action would pave the way for the development of desperately needed additional options to treat and maybe even prevent this devastating disorder.

We discovered that certain Human Milk Oligosaccharides (HMO) protect the breast-fed infant from NEC. Thus, we provide formulations containing such HMOs, methods and means for inhibiting bowel disease such as NEC.

SUMMARY OF THE INVENTION

In accordance with the present invention, novel formulations have been discovered that are useful for a variety of therapeutic applications. The invention provides formulations comprising isolated Disialyllacto-N-tetraose (DSLNT) or variants, isomers, analogs and derivatives thereof (DSLNT of the invention).

The invention also provides methods for preventing or treating a subject having a bowel disease and/or inflammation by administering Disialyllacto-N-tetraose (DSLNT) or variants, isomers, analogs and derivatives thereof in an amount sufficient to prevent or treat the bowel disease and/or inflammation in the subject.

The invention also provides methods of identifying whether a breast-fed infant is at risk of developing Necrotizing Enterocolitis (NEC) comprising measuring the concentration of Disialyllacto-N-tetraose (DSLNT) in the mother's milk, a low level of DSLNT being indicative that the breast-fed infant is at risk of developing NEC.

DETAILED DESCRIPTION OF THE INVENTION

Figure 1:
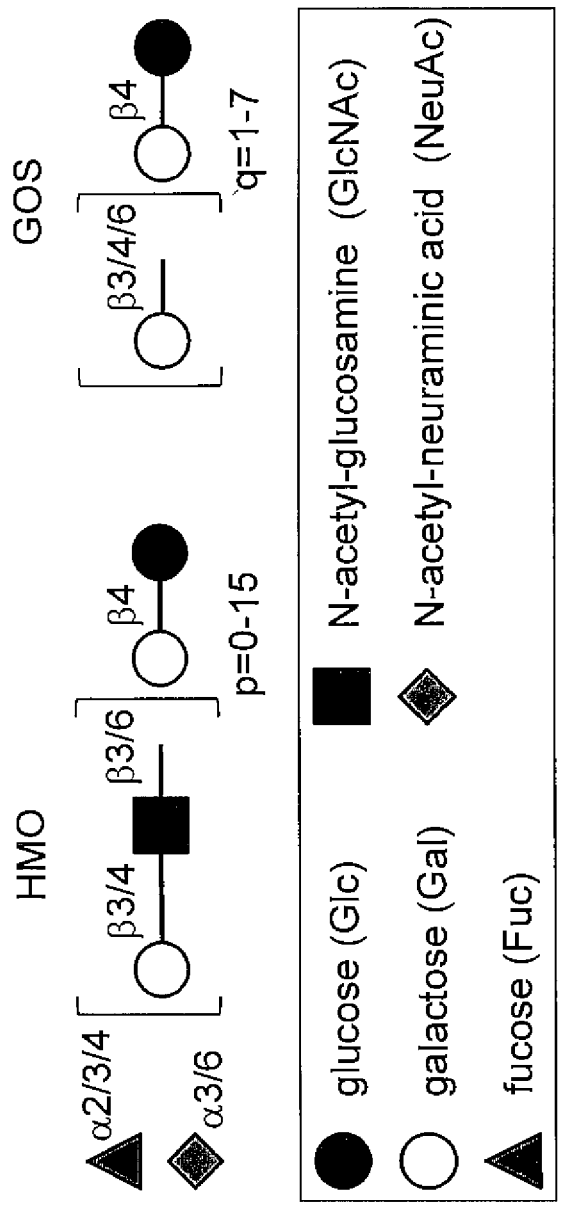
FIG. 1. HMO and GOS. Lactose (Galβ1-4Glc) forms the reducing end of Human Milk Oligosaccharides (HMO, left) and can be elongated at the non-reducing end by one or more lactosamine disaccharides (Galβ1-3/4GlcNAc), generating HMO of varying sizes. Lactose or the polylactosamine backbone can be modified by addition of fucose and/or by the addition of sialic acid (N-acetyl-neuraminic acid in humans) in various linkages. Each sialic acid contributes one negative charge to the HMO. Galactooligosaccharides (GOS, right) which are structurally very different from HMO, are elongated by galactose and lack fucose and sialic acid.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b. Unless otherwise indicated, all numbers expressing quantities of ingredients, properties such as molecular weight, reaction conditions, and so forth as used herein, are to be understood as being modified in all instances by the term "about." Accordingly, unless indicated to the contrary, the numerical parameters herein are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible.

Any numerical value, however, inherently contains standard deviations that necessarily result from the errors found in the numerical value's testing measurements.

As used herein, the terms "subject" and "patient" refer to any animal, such as a mammal. Mammals include but are not limited to, humans, murines, simians, felines, canines, equines, bovines, porcines, ovines, caprins, rabbits, mammalian farm animals, mammalian sport animals, and mammalian pets. In many embodiments, the hosts will be humans.

Isolated DSLNT and/or its variant, isomer, analog and/or derivative may be obtained by purifying DSLNT from nature or synthesized using known chemical or biochemical principles and methods. As used herein, the term "isolated" in reference to DSLNT of the invention does not require absolute purity.

I. Formulations of the Invention

The invention provides formulations comprising isolated Disialyllacto-N-tetraose (DSLNT) or variants, isomers, analogs and derivatives thereof (also referred to herein as DSLNT or DSLNT of the invention).

As used herein, Disialyllacto-N-tetraose (DSLNT) is also known as (2S,4S,5R,6R)-5-acetamido-2-[(2R,3R,4S,5S, 6R)-2-[(2R,3S,4R,5R,6S)-5-acetamido-2-[[(2R,4S,5R,6R)-5-acetamido-2-carboxylato-4-hydroxy-6-[(1R,2R)-1,2,3-trihydroxypropyl]oxan-2-yl]oxymethyl]-6-[(2R,3R,4S,5R, 6S)-3,5-dihydroxy-2-(hydroxymethyl)-6-[(2R,3S,4R,5R)-4, 5,6-trihydroxy-2-(hydroxymethyl)oxan-3-yl]oxy-oxan-4-yl]oxy-3-hydroxy-oxan-4-yl]oxy-3,5-dihydroxy-6-(hydroxymethyl)oxan-4-yl]oxy-4-hydroxy-6-[(1R,2R)-1,2, 3-trihydroxypropyl]oxane-2-carboxylate, or its synonyms, O—(N-acetyl-alpha-neuraminosyl)-(2-6)-O—(O—(N-acetyl-alpha-neuraminosyl)-(2-3)-beta-D-galactopyranosyl-(1-3))-O-2-(acetylamino)-2-deoxy-beta-D-glucopyranosyl-(1-3)-D-Glucose, α-Neu5Ac-(2→3)-β-Gal-(1→3)-[α-Neu5Ac-(2→6)]-β-GlcNAc-(1→6)-β-Gal-(1→4)-Glc, or Di-N-Acetylneuraminosyllacto-N-tetraose, with CAS registry number 61278-38-4.

An embodiment of DSLNT is shown in FIGS. 1, 4, 9E, and 10.

Figure 4:
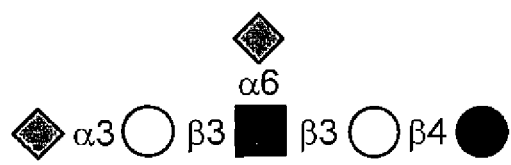
FIG. 4. Protective HMO #2 identified as Disialyllacto-N-tetraose. Glycan structure elucidation identified HMO #2 as a specific isomer of disialyllacto-N-tetraose (DSLNT).
Figure 4:
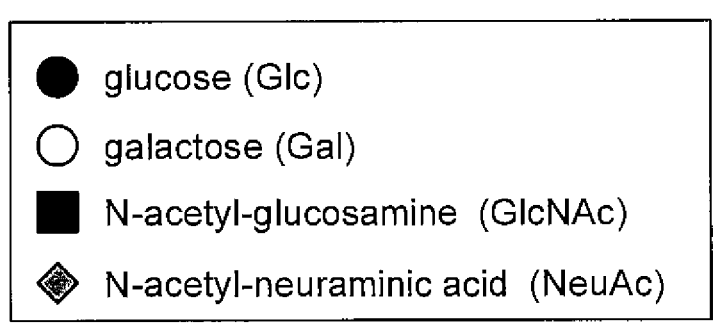

Derivatives, isomers, analogs and variants of DSLNT include oligosaccharides having (1) at least four sugar residues as in the lacto-N-tetraose (Galβ1-3GlcNAcβ1-3Galβ1-4Glc) backbone (e.g., as shown in FIG. 4), wherein the sugar can be any of D-glucose (Glc), D-galactose (Gal), L-fucose (Fuc), D-fructose (Fru), mannose (Man), N-acetyl-galactosamine (GalNAc) or N-acetyl-glucosamine (GlcNAc) and (2) a sialic acid (N-acetylneuraminic acid or Neu5Ac) residue at any two or more of the sugar residues. For example, a sialic acid residue may be attached at each of the first and second sugar residues with the terminal non-reducing sugar residue designated as the first sugar residue of the oligosaccharide. In another example, a sialic residue may be attached at each of the first and third sugar residues with the terminal non-reducing sugar residue designated as the first sugar residue of the oligosaccharide. However, the invention also contemplates that a sialic acid residue may be attached at any position including at the reducing end, e.g., Glc of DSLNT.

Merely by way of example, the DSLNT derivative may have four sugar residues such as a combination of glucose, galactose and N-acetyl-glucosamine and be modified with at least two sialic acid residues at any of the first three sugar subunits within the oligosaccharide chain in which the last final sugar would be glucose in the case of DSLNT or the corresponding sugar at this position in DSLNT variants, isomers, analogs and derivatives.

In another example, the DSLNT derivative may have four sugar residues, including a combination of glucose, galactose and N-acetyl-glucosamine (e.g., FIG. 4) and be modified with at least two sialic acid residues at any of the first three sugar subunits within the oligosaccharide chain.

In another example, the DSLNT derivative may have four sugar residues including a combination of glucose, fructose, galactose and N-acetyl-glucosamine and be modified with at least two sialic acid residues at any of the first three sugar subunits within the oligosaccharide chain.

In another example, the DSLNT variant, isomer, analog and derivative may have four glucose residues and be modified with at least two sialic acid residues at any of the first three sugar subunits within the oligosaccharide chain. In another example, the DSLNT derivative may have four fructose residues and be modified with at least two sialic acid residues at any of the first three sugar subunits within the oligosaccharide chain.

In another example, the DSLNT derivative may have four galactose residues and be modified with at least two sialic acid residues at any of the first three sugar subunits within the oligosaccharide chain.

In another example, the DSLNT derivative may have four N-acetyl-glucosamine residues and be modified with at least two sialic acid residues at any of the first three sugar subunits within the oligosaccharide chain.

In another example, the DSLNT derivative may have three galactose residues followed by a glucose residue, e.g., Gal-Gal-Gal-Glc, and be modified with at least two sialic acid residues at any of the first three sugar subunits within the oligosaccharide chain.

In another example, the DSLNT derivative may have three fructose residues followed by a glucose residue, e.g., Fru-Fru-Fru-Glc, and be modified with at least two sialic acid residues at any of the first three sugar subunits within the oligosaccharide chain.

While the derivatives may have any chemically permitted linkages for forming a covalent chemical bond or bonds between any two sugar molecules or monosaccharides, the preferred chemical linkages are: Neu5Ac residue linked in α2-3 or α2-6 linkage to Gal or GlcNAc residue; Fuc residue linked in α1-2, α1-3, or α1-4 linkage to Gal, GlcNAc, or Glc residue; Fm residue linked in β1-2, α1-2, to Fru, Gal, GlcNAc or Glc; GlcNAc residue linked in β1-3, β1-4, or β1-6 linkage to a Gal residue; and Gal residue linked in β1-3 or β1-4 linkage to a GlcNAc, Gal, or Glc residue. It is also preferred that the terminal sugar is a glucose residue, preferably linked to a galactose as in the disaccharide lactose.

Further, derivatives of DSLNT may be made by covalent linking of DSLNT to any other chemical compound or polymer, using methods known in the art of organic and synthetic chemistry or through enzymatic methods. These derivatives include but are not limited to attaching or covalent linking DSLNT to other oligosaccharides, amino acids, polypeptides, and nucleic acids.

Further, DSLNT variant, isomer, analog and derivatives may be made by substituting a sugar residue within DSLNT with a sugar analog. For example, galactose may be substituted with its analogs, including but not limited to 2-desoxy-D-galactose, 2-desoxy-2-fluoro-D-galactose and 2-desoxy-2-amino-D-galactose. For example, glucose may be substituted with its analogs, including but not limited to 2-Deoxy-D-glucose, 2,2-difluoro-deoxy-D-glucose, 2-deoxy-2-fluoro-2-iodo-D-glucose, 1-O-methyl-D-glucose, 2-O-methyl-D-glucose, 2-deoxy-2-chloro-D-glucose, 2-deoxy-2-bromo-D-glucose, 3-O-$^{11}$C-methyl-D-glucose, 6-deoxy-D-glucose, 6-deoxy-6-fluoro-D-glucose, and 6-deoxy-6-iodo-D-glucose, and 2-deoxy-2-$^{18}$F-fluoro-D-glucose. For example, N-acetylglucosamine may be substituted with its analogs, N-acetylglucosaminylasparagine, N-acetylglucosamine 6-sulfate, N-acetylglucosamine-1-phosphate, N-acetylglucosamine 6-phosphate, methyl-2-acetamido-2-deoxy-D-glucopyranoside, N-acetylglucosaminitol, N-bromoacetylglucosamine, 2-acetamido-1,3,6-tri-O-acetyl-4-deoxy-4-fluoroglucopyranose, N-acetylglucosamine thiazoline, N-fluoroacetyl-D-glucosamine, 2-acetamido-2-deoxy-D-glucono-(1,5)-lactone, and 3-acetamido-3,6-dideoxyglucose.

Furthermore isomers of DSLNT may be obtained based on a chiral center, such that D-glucose as a six member ring can exist either as α-D-glucopyranose or β-D-glucopyranose, depending on the orientation of the hydroxyl group at the C-1 position with respect to the rest of the ring. Similarly, D-galactose, N-acetylglucosamine and sialic acid rings may exist in either α- or β-conformation based on the hydroxyl group at the C-1 (for D-galactose and N-acetylglucosamine) and C-2 (for sialic acid) position with respect to the rest of the ring. The isomers of DSLNT may differ based on α- or β-position of the acetal functional groups. For example, the glycosidic linkage between galactose and glucose may be a-acetal functional group instead of β-acetal functional group as is normally found in lactose moiety of DSLNT. Thus, a number of isomers of DSLNT may exist based on the orientation of the hydroxyl-group at the C-1 or C-2 position of the six member rings. Some DSLNT isomers may include but are not limited to: α-Neu5Ac-(2→3)-α-Gal-(1→3)-[α-Neu5Ac-(2→6)]-β-GlcNAc-(1→3)-β-Gal-(1→4)-Glc, α-Neu5Ac-(2→3)-β-Gal-(1→3)-[α-Neu5Ac-(2→6)]-α-GlcNAc-(1→3)-β-Gal-(1→4)-Glc, α-Neu5Ac-(2→6)-β-Gal-(1→3)-[α-Neu5Ac-(2→6)]-β-GlcNAc-(1→2)-α-Gal-(1→4)-Glc, β-Neu5Ac-(2→3)-β-Gal-(1→3)-[α-Neu5Ac-(2→6)]-β-GlcNAc-(1→3)-β-Gal-(1→4)-Glc, or α-Neu5Ac-(2→3)-β-Gal-(1→3)-[β-Neu5Ac-(2→6)]-β-GlcNAc-(1→3)-β-Gal-(1→4)-Glc.

Since modification by sialic acid introduces a negative charge in form of a carboxyl-group (COO—), other monosaccharides also contain carboxyl-groups and may substitute for sialic acid in DSLNT variant, isomer, analog and derivatives. These sugars could be glucoronic acid, galacturonic acid, iduronic acids, 3-Deoxy-D-manno-oct-2-ulosonic acid, neuraminic acid, or any other carboxyl-group containing monosaccharides or derivatives thereof.

Variants, analogs and derivatives including its isomers and metabolites can be produced by modifying DSLNT through substitutions, modifications, and conjugations that preserve the biological activity of preventing or inhibiting a bowel disease, such as, for example, necrotizing enterocolitis, in a subject, e.g., a pediatric subject including infants, children, or adolescents. The subject may be a human or animal subject including a monkey, rat, mouse, dog, cat, pig, goat, sheep, horse or cow.

As used herein, suitable amounts of DSLNT (or variants, isomers, analogs and derivatives thereof) means an amount sufficient to inhibit a bowel disease. Examples of suitable amounts include, but are not limited to, an amount of about at least 30 μM, at least 300 μM, at least 600 μM, at least 800 μM, greater than 800 μM, in the range of approximately 10 μM-10,000 μM, approximately 600-1500 μM or approximately 500-800 μM dosage forms or compositions containing active ingredient (DSLNT of the invention) of about at least 38.7 mg/L, at least 387 mg/L, in the range of approximately 12.9 mg to 12.9 g per liter, approximately 774 mg/L to 1,935 mg/L, approximately 645 mg/L to 1,032 mg/L, or approximately 200-500 mg/L of DSLNT or derivative thereof with the balance made up from non-toxic carrier may be prepared. In some embodiments, these amounts or ranges may vary by about 10%. In other embodiments, the amounts or ranges may vary by about 20%. In still other embodiments, these amounts or ranges may vary by about 25%. Methods for preparation of these compositions are known to those skilled in the art.

In one embodiment, the present formulation comprises about 387 mg/L (~300 μM) DSLNT of the invention.

The formulation of the invention preferably comprises other components, such as vitamins and/or minerals, preferably according to international directives for infant formulae.

The concentration of DSLNT of the invention in the formulation will depend on absorption, inactivation and excretion rates of the DSLNT of the invention, the dosage schedule, and amount administered as well as other factors known to those of skill in the art. The concentrations of the DSLNT of the invention are effective for delivery of an amount, upon administration, that treats, prevents, or ameliorates one or more of the symptoms of diseases or disorders to be treated.

In the formulations, DSLNT of the invention can also be mixed with other mammalian or plant proteins. For example, mammalian proteins include proteins from mammalian milk (e.g., either intact or partial protein hydrolysates of whole or fractionated mammalian milk). Plant proteins include intact protein or protein hydrolysate from pea, soy, almond, and/or rice proteins. In the formulation, the weight fraction of the DSLNT of the invention may be dissolved, suspended, dispersed or otherwise mixed in a selected carrier at an effective concentration such that the treated condition is relieved, prevented, or one or more symptoms are ameliorated.

In one embodiment, the formulation of the invention is an enteral formulation. Enteral formulations of the invention may be embodied in an infant formula, breast milk, water, juices, or baby food. Additionally, enteral formulations of the invention may be embodied in a nutritional supplement.

In the formulations of the invention, DSLNT can also be mixed with other mammalian or plant proteins. For example, mammalian proteins include proteins from mammalian milk e.g., either intact or partial protein hydrolysates of whole or fractionated mammalian milk. Plant proteins include intact protein or protein hydrolysate from pea, soy, almond, and/or rice proteins.

In a further embodiment, the formulation of the invention may be added to any liquid for consumption. Liquids include, but are not limited to, water or juices.

In another embodiment, the formulation of the invention is used to supplement or fortify the mother's own milk or human donor milk (human milk fortifier) with DSLNT and/or its derivatives, isomers, analogs. Commercial pasteurized human donor milk may be obtained from Prolacta Bioscience (Monrovia, Calif.) under the name Prolact+H$^2$MF such as Prolact+4®, Prolact+6®, Prolact+8®, and Prolact+10®. Fortification of mother's milk may be performed with or without prior knowledge of the DSLNT content of the mother's milk and would be warranted in the case of low DSLNT levels in either mother's own milk or donor milk.

The present invention additionally provides pharmaceutical formulations (also known as pharmaceutical compositions or dosage forms) comprising isolated DSLNT and/or its derivatives, isomers, analogs and/or variants, and a pharmaceutically acceptable excipient or vehicle.

In one embodiment, the formulation of the invention comprises isolated DSLNT or variants, isomers, analogs and derivatives thereof and a pharmaceutical acceptable excipient.

In another embodiment, the formulation of the invention consists of isolated DSLNT or variants, isomers, analogs and derivatives thereof and a pharmaceutical acceptable excipient.

In yet another embodiment, the formulation of the invention comprises isolated DSLNT or variants, isomers, analogs and derivatives thereof and a pharmaceutical acceptable excipient but is substantially free of other oligosaccharides (e.g. non-DSLNT oligosaccharides).

Pharmaceutically acceptable excipient or vehicle refers to a non-toxic solid, semisolid (also referred to herein as softgel) or liquid filler, diluent, encapsulating material or formulation auxiliary of any type.

Further, isolated DSLNT and/or its derivatives, isomers, analogs and/or variants of the invention can be pegylated, phosphorylated, esterified, derivatized with amino acids and/or peptides, to improve solubility for both formulation and bioavailability.

The isolated DSLNT and/or its derivatives, isomers, analogs and/or variants of the present invention may be mixed with pharmaceutically acceptable excipients. Examples of excipients include but are not limited to binders, diluents, adjuvants, or vehicles, such as preserving agents, fillers, polymers, disintegrating agents, glidants, welling agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable excipients are generally non-toxic to recipients at the dosages and concentrations employed and are compatible with other ingredients of the formulation. Examples of pharmaceutically acceptable excipients include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polvinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Hom, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225).

Examples of disintegrating agents include, but are not limited to, complex silicates, croscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to the active agents (DSLNT of the invention), while maintaining effectiveness of the formulations in treating the bowel disease e.g., NEC. The list provided herein is not exhaustive.

The formulation of the invention may be administered orally (e.g., in liquid form within a solvent such as an aqueous or non-aqueous liquid, or within a solid carrier), rectally, parenterally, intracisternally, intravaginally, intraperitoneally, topically (as by powders, ointments, lotion, gels, drops, transdermal patch or transcutaneous patch), bucally, in bronchial form or as an oral or nasal spray. The term "parenteral" as used herein refers to modes of administration which include intravenous (e.g., within a dextrose or saline solution), intramuscular, intrasternal, subcutaneous, intracutaneous, intrasynovial, intrathecal, periostal, intracerebroventricularly, intra-articular injection and/or infusion. Administration can be performed daily, weekly, monthly, every other month, quarterly or any other schedule of administration as a single dose injection or infusion, multiple doses, or in continuous dose form. The administration of the formulation of the present invention can be intermittent or at a gradual, continuous, constant or controlled rate to a subject. In addition, the time of day and the number of times per day that dosage form(s) is administered can vary.

The appropriate dose of the compound will be that amount effective to prevent occurrence of a bowel disease. By "effective amount", "therapeutic amount" or "effective dose" is meant that amount sufficient to elicit the desired pharmacological or therapeutic effects, thus resulting in effective prevention or treatment of the disorder or condition.

The isolated DSLNT or variants, isomers, analogs and derivatives thereof of the invention may be also formulated into suitable pharmaceutical preparations such as solutions, suspensions, tablets, dispersible tablets, pills, capsules, powders, sustained release formulations or elixirs, for oral administration.

Oral formulations may be solid, gel or liquid. The solid dosage forms include tablets, capsules, granules, and bulk powders. Liquid formulations can, for example, be prepared by dissolving, dispersing, or otherwise mixing isolated DSLNT of the invention as defined above and pharmaceutical adjuvants in a carrier, such as, for example, water, saline, aqueous dextrose, glycerol, glycols, ethanol, and the like, to thereby form a solution or suspension. If desired, the formulation of the invention to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, and mannitol and dicalcium phosphate.

Glidants include, but are not limited to, colloidal silicon dioxide. Disintegrating agents include crpsscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors.

Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammuoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active material, isolated DSLNT of the invention, can also be mixed with other mammalian or plant proteins. For example, mammalian proteins include proteins from mammalian milk (e.g., either intact or partial protein hydrolysates of whole or fractionated mammalian milk). Plant proteins include intact protein or protein hydrolysate from pea, soy, almond, and/or rice proteins.

Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are well known in the art. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells.

Of interest herein are also powders, which can be reconstituted for administration as solutions, emulsions and other mixtures. They may also be reconstituted and formulated as solids or gels.

Isolated DSLNT may reduce the risk of NEC through its action as a prebiotic, promoting the growth of beneficial bacteria such as *Bifidobacteria* and *Lactobacilli* while reducing the load of pathogenic bacteria that cause bowel diseases. As such, isolated DSLNT and its variants, isomers, analogs and derivatives may serve as a prebiotic, which selectively stimulates the growth or colonization of one or more bacterial species in the gastrointestinal tract of a host and presence of these bacteria are beneficial to the health of the host.

As a prebiotic, isolated DSLNT and/or its derivatives, isomers, analogs and/or variants may be administered with a probiotic, which can be live or dead microorganisms conferring a health benefit to the host when administered in sufficient quantity. Microorganisms considered to have health benefit to its host include but are not limited to those belonging to the genera, *Bifidobacteria* and *Lactobacilli*. Although the probiotic can have either live or dead microorganism, it is generally preferably to live microorganism ingested by the subject as a probiotic. The probiotic may take on a number of different forms, such as powder, freeze-dried cells, bar, liquid culture, concentrated liquid culture, paste, yogurts, or combinations thereof. Enteral administration or liquid feeding are preferred routes for introducing probiotic along with DSLNT and its derivatives, isomers, analogs and variants to newborns.

The probiotic in powder, liquid or bar form may be included into a nutritional formula, as described hereinafter. The compositions may comprise any amount of *Bifidobacteria* and/or *Lactobacilli* probiotic effective for treating and/or preventing NEC or bowel disease when enterally administered to an individual in combination with the prebiotic of the present disclosure. Typically, the compositions will comprise probiotic in sufficient amounts to provide a daily dose of e.g. from about $10^6$ colony forming units (cfu) to about $10^{12}$ colony forming unit (cfu), or from about $10^6$ cfu to about $10^{10}$ cfu, or from about $10^8$ cfu to about $10^{12}$ cfu, or from about $10^8$ cfu to about $10^{10}$ cfu of probiotic to an individual upon ingestion of the composition. In some embodiments, the compositions will comprise probiotic sufficient to provide a daily dose of about $10^6$ cfu, or about $10^7$ cfu, or about $10^8$ cfu, or about $10^9$ cfu, or about $10^{10}$ cfu, or about $10^{11}$ cfu or about $10^{12}$ cfu to an individual upon ingestion of the composition.

In a nutritional formula, the nutritional formula may comprise: 1) DSLNT and/or its derivatives, isomers, analogs and/or variants, and 2) probiotic microorganism from about $10^4$ cfu to about $10^{10}$ cfu of probiotic per gram dry weight of the nutritional formula, or from about $10^4$ cfu to about $10^9$ cfu per gram dry weight of the nutritional formula, or from about $10^4$ cfu to about $10^8$ cfu of probiotic per gram dry weight of the nutritional formula, or from about $10^4$ cfu to about $10^7$ cfu of probiotic per gram dry weight of the nutritional formula, or from about $10^4$ cfu to about $10^6$ cfu of probiotic per gram dry weight of the nutritional formula, or from about $10^4$ cfu to about $10^5$ cfu of probiotic per gram dry weight of the nutritional formula. In another embodiment, the nutritional formula may comprise from about $10^6$ cfu to about $10^8$ cfu of probiotic per gram dry weight of the nutritional formula, or from about $10^6$ cfu to about $10^7$ cfu of probiotic per gram dry weight of the nutritional formula. In another embodiment, the nutritional formula may comprise about $10^4$ cfu of probiotic per gram dry weight of the nutritional formula, or about $10^5$ cfu of probiotic per gram dry weight of the nutritional formula, or about $10^6$ cfu of probiotic per gram dry weight of the nutritional formula, or about $10^7$ cfu of probiotic per gram dry weight of the nutritional formula, or about $10^8$ cfu of probiotic per gram dry weight of the nutritional formula, or about $10^9$ cfu of probiotic per gram dry weight of the nutritional formula, or about $10^{10}$ cfu of probiotic per gram dry weight of the nutritional formula.

DSLNT of the invention can be derived using any number of sources and methods known to those of skill in the art. Alternatively, DSLNT of the invention can be synthesized by enzymatic methods, using isolated oligosaccharide biosynthetic enzyme or catabolic enzyme that participate in the biosynthesis or catabolism of DSLNT of the invention in either forward or reverse reaction, respectively; or alternatively, DSLNT derivatives, analogs, and variants can be derived by replacing key enzymatic steps with a different biosynthetic or catabolic enzyme and desired sugar analog to obtain the desired oligosaccharide. DSLNT of the invention can also be synthesized by chemical methods and purified to obtain the desired compounds.

The prebiotic and probiotic combination composition may be in powder or liquid form and/or may be included into a nutritional or infant formula. The compositions may comprise any amount of prebiotic DSLNT and/or its derivatives, isomers, analogs and/or variants effective for treating and/or preventing NEC or bowel disease when enterally administered to an individual in combination with a probiotic, such as bacterial species from the genera, *Bifidobacteria* and/or *Lactobacilli*.

When the combination of prebiotic DSLNT and/or its derivatives, isomers, analogs and/or variants and probiotic, such as bacterial species from the genera, *Bifidobacteria* and/or *Lactobacilli*, is formulated as a nutritional or infant formula, the nutritional or infant formula may comprise from about 0.35 grams prebiotic per 100 grams nutritional to about 9.2 grams prebiotic per 100 grams nutritional, or from about 1.5 grams prebiotic per 100 grams nutritional to about 7.0 grams prebiotic per 100 grams nutritional, or from about 1.5 grams prebiotic per 100 grams nutritional to about 6.0 grams prebiotic per 100 grams nutritional. And preferably from about 3.0 grams prebiotic per 100 grams nutritional to about 6.0 grams prebiotic to about 100 grams nutritional.

In one embodiment, DSLNT and/or its derivatives, isomers, analogs and/or variants may be administered to a subject or patient as a prebiotic to stimulate colonization or growth of *Bifidobacteria* and *Lactobacilli* in the gastrointestinal tract and reducing the presence of pathogens.

In another embodiment, DSLNT and/or its derivatives, isomers, analogs and/or variants may be administered to a subject or patient along with a probiotic, such as *Bifidobacteria* and *Lactobacilli*, to help establish a healthy gastrointestinal tract microbial flora.

II. Methods of the Invention

The invention also provides method of preventing or treating a subject having a bowel disease and/or inflammation by administering isolated Disialyllacto-N-tetraose (DSLNT) or variants, isomers, analogs and derivatives thereof in an amount sufficient to prevent or treat the bowel disease and/or inflammation in the subject.

Examples of bowel diseases and inflammatory diseases include but are not limited to Necrotizing Enterocolitis (NEC), ulcerative colitis, Crohn's disease, collagenous colitis, lymphocytic colitis, ischaemic colitis, diversion colitis, Behçet's disease, indeterminate colitis, microscopic colitis, pouchitis, pseudomembranous colitis, ischemic colitis, diverticulitis, inflammatory bowel disease, appendicitis, and irritable bowel syndrome.

The phrase "treating" or "treatment" refers to any manner in which one or more of the symptoms of a disease or disorder are ameliorated or otherwise beneficially altered, whether in a permanent or temporary manner, which can be attributed to or associated with administration of the formulation herein. The term encompasses any pharmaceutical use, including prophylactic uses in which the development of one or more of the symptoms of a disease or disorder is prevented, delayed or reduced, whether in a permanent or temporary manner, which can be attributed to or associated with administration of the formulation of the invention.

The subject may be a human or animal subject including a monkey, rat, mouse, dog, cat, pig, goat, sheep, horse or cow. Preferably, the subject is a pediatric subject including infants, children, and adolescents. The subject may be suffering from diarrhea, enteritis, colitis, cramping, abdominal pain, edema, ulcer, gastritis, intestinal disease, digestive disease or inflammatory bowel disease. In one embodiment, the bowel disease is an infectious disease. In another embodiment, the bowel disease is Necrotizing Enterocolitis (NEC).

In accordance with the practice of the invention, the formula of the invention may be a liquid formula (e.g., an infant formula), or a solid or semi-solid formula (e.g., baby food or nutritional supplement) that is given by mouth. However, other administrations means are possible and encompassed by the invention.

Additionally, DSLNT of the invention may also be administered by means of animal feed, animal feed supplement, or animal nutritional supplement.

The invention further provides methods of identifying whether a breast-fed infant is at risk of developing Necrotizing Enterocolitis (NEC). In one embodiment, the method comprises measuring the concentration of DSLNT in the mother's milk, a low level of DSLNT being indicative that the breast-fed infant is at risk of developing NEC. Merely as an example, low levels of DSLNT may be established by measuring the concentration of DSLNT in mother's milk and total amount of daily DSLNT intake, and comparing these values with the incidence of NEC in newborns.

III. Kits

According to another aspect of the invention, kits are provided. Kits according to the invention include package(s) comprising formulations of the invention.

The phrase "package" means any vessel containing compounds or compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering formulations of the present invention to a subject having a condition in need of treatment. Kits may also comprise instructions for approved uses of compounds herein by regulatory agencies, such as the United States Food and Drug Administration. Kits may optionally contain labeling or product inserts for the present compounds. The package(s) and/or any product insert(s) may themselves be approved by regulatory agencies. The kits can include compounds in the solid phase or in a liquid phase (such as buffers provided) in a package. The kits also can include buffers for preparing solutions for conducting the methods, and pipettes for transferring liquids from one container to another.

In a further embodiment, the present invention provides kits (i.e., a packaged combination of reagents with instructions) containing the DSLNT and/or its derivatives, isomers, analogs and/or variants of the invention useful for treating a bowel disease (e.g., NEC).

The kit can contain a formulation of the invention that includes one or more agents of the invention effective for treating a bowel disease and an acceptable carrier or adjuvant, e.g., pharmaceutically acceptable buffer, such as phosphate-buffered saline, Ringer's solution or dextrose solution.

It may further include other materials desirable from a commercial and user standpoint, including other buffers; diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the DSLNT and/or its derivatives, isomers, analogs and/or variants for example, dissolving of the dry powders, and/or treatment for e.g. a bowel disease (such as NEC).

The label and/or the instructions can indicate directions for in vivo use of the formulation of the invention. The label and/or the instructions can indicate that the formulation of the invention is used alone, or in combination with another agent to treat e.g., a bowel disease (such as NEC).

The label can indicate appropriate dosages for the DSLNT and/or its derivatives, isomers, analogs and/or variants of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

The following examples are provided to further illustrate aspects of the invention. These examples are non-limiting and should not be construed as limiting any aspect of the invention.

EXAMPLES

Example 1

Human Milk Oligosaccharides (HMO) Prevent NEC in Neonatal Rats

In addition to lactose, one liter of mature human milk contains 5-15 g of unbound oligosaccharides, which is similar to the total amount of milk proteins and exceeds the amount of milk lipids. FIG. 1 shows that HMO are a heterogeneous group of oligosaccharides that vary in charge depending on the number of sialic acids per HMO molecule as well as in size depending on the length of the polylactosamine backbone. More than 150 different HMO have been identified. In contrast, infant formula contains much lower amounts of oligosaccharides, which are also structurally less complex. To compensate for the lack of HMO, formula is now often supplemented with Galactooligosaccharides (GOS), which partially mimic the prebiotic effect of HMO. However, as shown in FIG. 1, GOS are structurally very different from HMO and likely unable to also mimic the more structure-specific effects of HMO.

Figure 2:
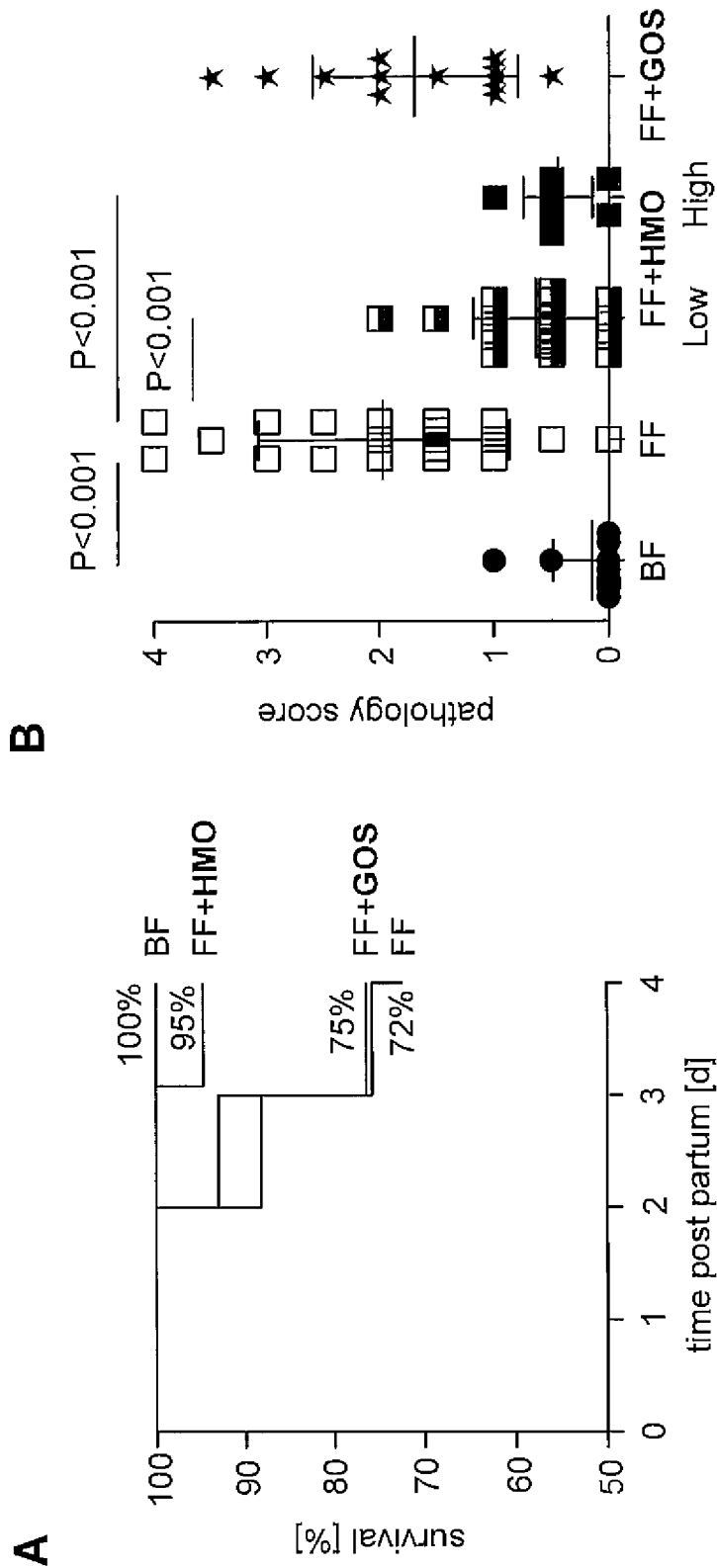
FIG. 2. HMO prevent NEC in neonatal rats A: Four-day survival. HMO (10 mg/mL) restored survival rates while GOS (8 mg/mL) had no effect. Note that x-axis intersects at 50% survival. B: Pathology scores of H&E-stained ileum sections (0: healthy; 4: complete destruction). Addition of HMO at low (1 mg/mL) and high concentrations (10 mg/mL) significantly reduced scores. GOS (8 mg/mL) had no effect. Each point represents one animal. Lines represent mean and standard deviation. [BF: breast-fed; FF: formula-fed].

Although a beneficial effect of HMO on NEC has been hypothesized, the limited availability of HMO make controlled and statistically powered intervention studies on human preterm infants unfeasible. Instead, we tested HMO in a well-established NEC model with neonatal Sprague-Dawley rats. We induced time-pregnant rats by oxytocin and randomized their pups into the different intervention groups. Some pups were left with the dam to serve as breast-fed controls; others were formula-fed by oral gavage twice daily. All pups were exposed to hypoxia thrice daily. On day-of-life 4, we sacrificed the pups and analyzed their intestines for macroscopic and microscopic signs of NEC. The ileum was prepared for H&E staining and evaluated blindly by three independent investigators to determine NEC pathology scores. While all breast-fed pups survived until day 4, the survival rate dropped to 72% in formula-fed pups (FIG. 2A). In parallel, NEC pathology scores increased significantly (FIG. 2B). We then isolated HMO from pooled human milk and added them to the formula. Survival rates and pathology scores significantly improved and were similar to breast-fed controls. These results show for the first time that HMO indeed prevent NEC in an animal model. Adding GOS had no effect on survival and pathology scores, suggesting that the beneficial effects of HMO might not simply be prebiotic in nature and more structure-specific.

One Specific HMO Prevents NEC in Neonatal Rats

HMO are a structurally heterogeneous group of oligosaccharides, triggering the question whether all HMO have similar effects in preventing NEC or whether the beneficial effects are based on distinct structural features. We separated the pooled HMO by two-dimensional glycan chromatography, and tested whether the fractions and subtractions reduce NEC in rats.

Figure 3:
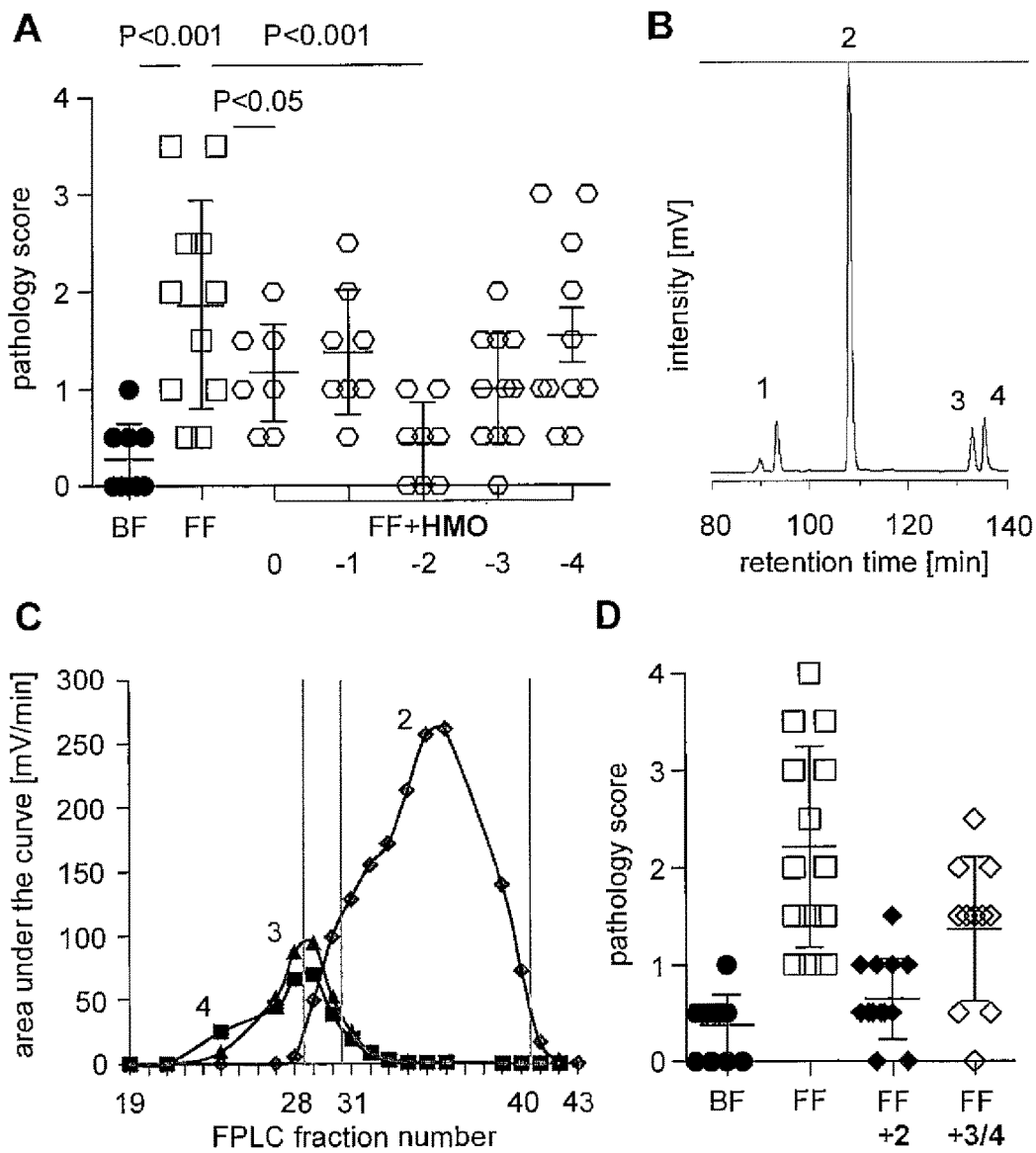
FIG. 3. Two-dimensional chromatography identifies most effective HMO. A: Rat NEC after HMO fractionation by charge. Pooled HMOs were fractionated by QAE based on charge. HMOs that contain no sialic acid carry no charge (0). HMOs with one or more sialic acids carry one or more negative charges (−1, −2, . . . ). The QAE-2 fraction was most effective in preventing NEC. B: HPLC-FL showed QAE-2 contained only 4 major oligosaccharides. #1 is a monosialylated HMO, which was considered an irrelevant spill-over from the QAE-1 fraction, which was ineffective. C: FPLC P2 subfractionation by size. Fractions containing only #2 (31-40) were pooled and separated from fractions containing only #3 and #4. #3 and #4 could not be separated from each other. Loss in the excluded fractions was considered accordingly. D: Rat NEC after FPLC subfractionation. While #3 and #4 had no effect, #2 significantly reduced NEC. [BF: breast-fed; FF: formula-fed].

In the first dimension, we used anion exchange chromatography (QAE) to separate the HMO by charge based on the number of sialic acids per HMO molecule. The neutral fraction with no sialic acid slightly reduced NEC pathology scores (FIG. 3A). Monosialylated HMO (−1), which comprise about 90% of all sialylated HMO, had no effect, but the disialylated HMO (−2) significantly reduced scores comparable to breast-fed controls. Tri- (−3) and tetrasialylated HMO (−4) were ineffective, probably due to their extremely low abundance. We used HPLC-FL of fluorescently tagged HMO and showed that the disialylated HMO contained only four major oligosaccharides (FIG. 3B). One of them (#1) was identified as a minor monosialylated HMO spill-over, which we disregarded.

In the second dimension, we used FPLC size exclusion chromatography to further separate the disialylated HMO fraction by size (FIG. 3C). We were able to separate HMO #2 from HMO #3 and 4. HMO #3 and 4 did not prevent NEC (FIG. 3D). However, HMO #2 significantly reduced NEC pathology scores.

Each HMO fraction and subfraction was tested at concentrations that were based on their relative abundance in pooled HMO at 10 mg/mL, the average concentration in mature human milk. Assuming an average molecular weight of 1,000 g/mol for pooled HMO, 10 mg/mL is equivalent to 10 mM. The relative abundance of the protective HMO #2 was ~3%, which corresponds to 300 µM and is well within the range of other previously reported bioactive glycans. In conclusion, we identified one specific HMO that prevents NEC in a neonatal rat model at biologically relevant concentrations. Next, we elucidated the structural composition of this particular HMO.

Glycan Structure Elucidation Identifies DSLNT as Protective HMO

We collaborated with the UC San Diego Glycotechnology Core to elucidate the monosaccharide composition, sequence and glycosidic linkages of the protective HMO #2. MALDI-TOF-MS analysis suggested the presence of three hexoses, one hexosamine and, as expected, two sialic acids. Sequential digestion with linkage-specific exoglycosidases as well as GC-MS analysis of permethylated derivatives revealed lacto-N-tetraose (Galβ1-3GlNAcβ-3Galβ1-4Glc) as the backbone (FIG. 4) with one sialic acid α2-3-linked to the terminal Gal and the other sialic acid α2-6-linked to the subterminal GlcNAc. Our approach unambiguously identified HMO #2 as a specific isomer of disialyllacto-N-tetraose (DSLNT).

Example 2

Materials and Methods
Isolation of Pooled HMO

Human milk was obtained from 12 healthy volunteers of preterm infants recruited at the University of California—San Diego Medical Center, San Diego, Calif., USA, after approval by the university's institutional review board. After centrifugation, the lipid layer was removed and proteins were precipitated from the aqueous phase by addition of ice-cold ethanol and subsequent centrifugation. Ethanol was removed from the HMO-containing supernatant by roto-evaporation. Lactose and salts were removed by gel filtration chromatography over a BioRad P2 column (100 cm×16 mm, Bio-Rad, Hercules, Calif., USA) using a semi-automated fast protein liquid chromatography (FPLC) system. GOS syrup (Vivinal, dry matter 75%) was provided by Friesland Campina Domo (Amersfoort, The Netherlands). Disialyllacto-N-tetraose (DSLNT) was purchased from Dextra (Reading, UK).

HMO Fractionation by Two-Dimensional Chromatography

Pooled HMO were separated by charge using anion exchange chromatography over QAE gravity columns (Sigma Aldrich, St. Louis, Mo., USA). Lyophilized pooled HMO were dissolved in 2 mM Tris and applied to equilibrated columns. Neutral, −1, −2, −3 and −4 charged HMO were eluted with 2 mM Tris containing 0, 20, 70, 100 and 400 mM NaCl, respectively. Tris and NaCl were removed by gel filtration chromatography over a P2 column. Separation was monitored by fluorescence high-performance liquid chromatography (HPLC-FL) as described below. Differently charged HMO fractions were further separated by size using P2 gel filtration chromatography (100 cm×16 mm) and monitored by HPLC-FL. Fractions that contained the same, but no other HMO were pooled and lyophilized.

Oligosaccharide Profiling by HPLC

HMO and GOS were fluorescently labelled with 2-aminobenzamide (2AB) and separated by HPLC on an amide-80 column (4.6 mm ID×25 cm, 5 µm, Tosoh Bioscience, Tokyo, Japan) with a 50 mM ammonium formate/acetonitrile buffer system. Separation was monitored by a fluorescence detector at 360 nm excitation and 425 nm emission. Peak annotation was based on standard retention times and mass spectrometric (MS) analysis on a Thermo LCQ Duo Ion trap mass spectrometer equipped with a Nano-ESI-source.

HMO Analysis by MALDI-TOF Mass Spectrometry

2AB-labelled HMO peaks were collected, dried and mixed with super-DHB matrix in a 1:1 ratio and spotted on MALDI plates for analysis. Spectra were acquired in positive ion mode.

HMO Analysis by Sequential Exoglycosidase Digest

Linkage promiscuous neuraminidase (α2-3>6,8,9; *Arthrobacter ureafaciens*) was purchased from Sigma Aldrich (St. Louis, Mo., USA); α2-3-specific neuraminidase (*Salmonella typhimurium*), β1-3 galactosidase (*Xanthomonas manihotis*), β1-4 galactosidase (*Bacteroides fragilis*) and β-N-acetyl-glucosaminidase (GlcNAcase, *X manihotis*) were obtained from New England Biolabs (Ipswich, Mass., USA). All enzymes were used at concentrations and incubation times according to the manufacturers' protocols.

HMO Linkage Analysis by Gas Chromatography Mass Spectrometry (GC-MS)

The unknown HMO 2 was dissolved in dimethylsulphoxide and par-O-methylated by sequential addition of sodium hydroxide and methyl iodine. Chloroform was added and the reaction stopped by the addition of water. The methylated glycan was extracted in the chloroform layer, dried and hydrolyzed with 4N trifluoroacetic acid at 100° C. for 6 h. Acids were removed with 50% isopropanol:water under dry nitrogen flush. Hydrolyzed samples were reduced overnight by sodium borohydride in 1M ammonium hydroxide. Excess borohydride was neutralized by 30% acetic acid and boric acid was removed as methyl borate. Samples were treated with 1:1 acetic anhydride:pyridine at 100° C. for 1 h. Pyridine and acetic anhydride were removed by nitrogen flush. Partially methylated alditol acetates were extracted with dichloromethane, analyzed by GC-MS with a DB-5 capillary column, and identified by a combination of established retention times and mass fragmentation patterns.

Induction and Evaluation of NEC in Neonatal Rats

The NEC model in neonatal rats was originally described by Barlow et al. (Surgery 1975; 77:687-90) and later modified (Nadler E P, Dickinson E, Knisely A, et al., J Surg Res 2000; 92:71-7). Briefly, pregnant time-dated Sprague-Dawley rats were induced at term using Pitocin (1-2 U per animal). Immediately after birth, neonates were randomized into one of the different study groups. Animals in the dam-fed (DF) group remained with the dam. All other animals were separated from the dam, housed in a temperature- and humidity-controlled incubator and orally gavaged with a special rodent formula (0.2 ml) twice daily. The formula approximates the protein and caloric content of rat breast milk and consists of 15 g Similac 60/40 (Ross Pediatrics, Columbus, Ohio, USA) in 75 ml of Esbilac canine milk replacer (Pet-Ag, Hampshire, Ill., USA). All animals, dam-fed and gavaged, were exposed to 10 min of hypoxia (5% $O_2$, 95% $N_2$) thrice daily in a modular chamber. All animals were sacrificed 96 h post-partum; their intestines were collected and inspected for the presence of gross necrotic changes or *Pneumatosis intestinalis*. A 0.5 cm section of the terminal ileum was prepared for H&E staining per standard protocols and scored blindly by three investigators based on morphological changes that included epithelial sloughing, villus oedema, infiltration of neutrophils, apoptosis of villus enterocytes, crypt hyperplasia and misaligned nuclei in the epithelium. If at least one pathology sign was observed, a score of 0.5-1.5 was assigned depending on severity. Two or three signs together resulted in a score of 2-3. The maximum score of 4 was given in case of complete obliteration of the epithelium with or without intestinal perforation. Pathology scores were plotted for each animal and the mean calculated per group. Each intervention was tested in at least two independent sets of experiments with a total of 8-26 animals per intervention group. Differences between the groups were calculated by one-way ANOVA with the Kruskal-Wallis test and Dunn's multiple comparison test. Significance was defined as $p<0.05$.

Results

Pooled HMO, but not GOS Improve Survival and Reduce NEC in Neonatal Rats

Figures 1, 5:
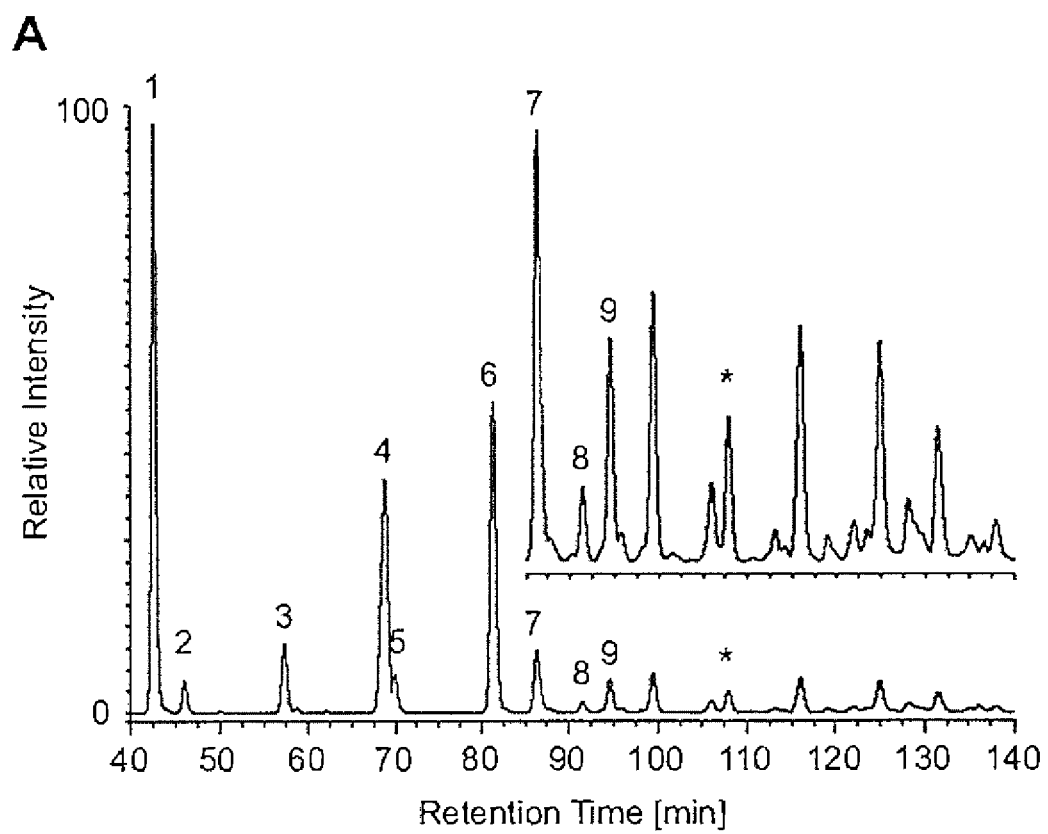
FIG. 5. Human milk oligosaccharides (HMO) and galacto-oligosaccharides (GOS) are structurally different (A) Fluorescence high-performance liquid chromatography (HPLC-FL) chromatogram of 2AB-labelled HMO isolated from pooled human milk. Most common HMO are annotated and listed in panel B. *Disialyllacto-N-tetraose (DSLNT), which was later identified as the NEC-protective HMO. (B) Schematic representation of the most common oligosaccharides found in the isolated pooled HMO. Numbers in brackets correspond to the annotated peaks in panel A. 2'FL, 2'-fucosyllactose; 3FL, 3-fucosyllactose; 3'SL, 3'-sialyllactose; LNT, lacto-N-tetraose; LNnT, lacto-N-neotetraose; LNFP1, lacto-N-fucopentaose 1; LNFP2, lacto-N-fucopentaose 2; LSTb, sialyllacto-N-tetraose b; LSTc, sialyllacto-N-tetraose c. Monosaccharide key: dark circle, glucose (Glc); light circle, galactose (Gal); square, N-acetyl-glucosamine (GlcNAc); triangle, fucose (Fuc); diamond, N-acetyl-neuraminic acid (NeuAc). (C) HPLC-FL chromatogram of Vivinal GOS, Peak clusters represent structural isomers of oligosaccharides with the same degree of polymerization and depend on the number of galactose residues per GOS molecule. Comparison of the HMO and GOS chromatograms confirmed a clear difference in the structural composition.
Figures 2, 5:
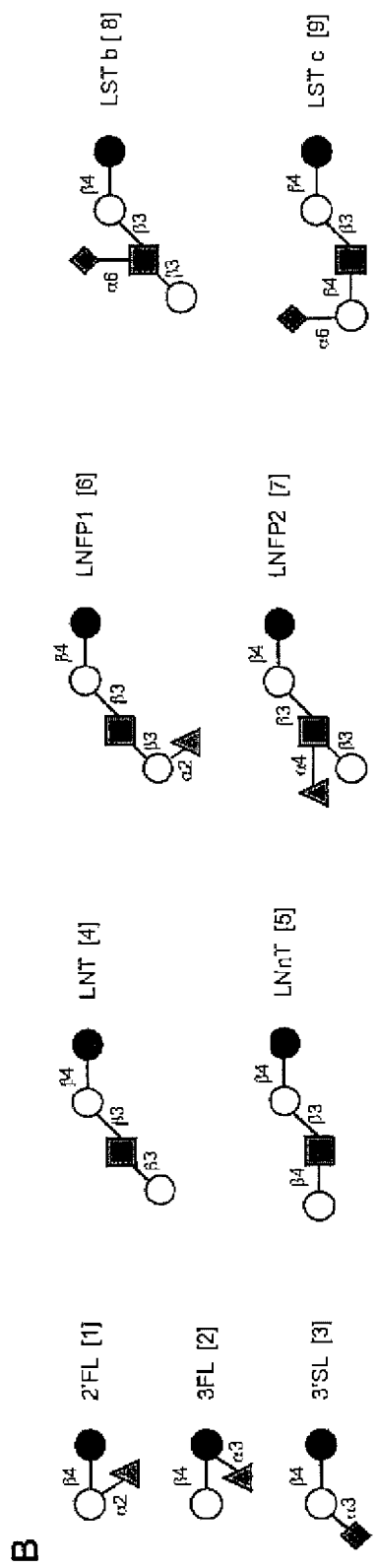
Figures 3, 5:
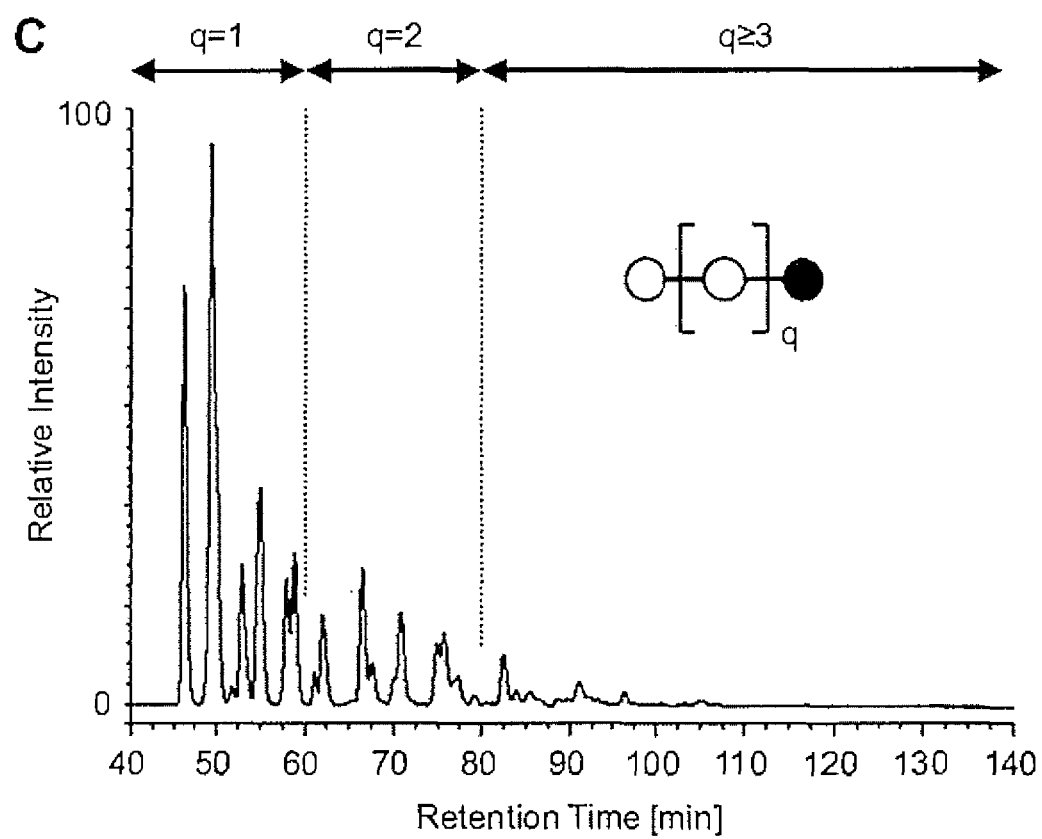

The primary objective of this study was to assess whether HMO affect NEC in neonatal rats. Therefore, we randomized rat pups at birth into different study groups. The first group stayed with the dam for the entire duration of the study (dam-fed, DF), but was exposed to hypoxia thrice a day together with all the other groups. The second group was fed formula that did not contain HMO (formula-fed, FF). The third group was fed formula supplemented with HMO at 10 mg/ml (FF+HMO), the average HMO concentration in mature human milk. The fourth group was fed formula supplemented with GOS at 8 mg/ml (FF+GOS), comparable to the GOS concentration in infant formula with prebiotics. HPLC-FL analysis of the isolated, pooled HMO showed that 2'-fucosyllactose (2'FL), lacto-N-fucopentaose 1 (LNFP 1) and lacto-N-tetraose (LNT) were the major oligosaccharides (FIG. 5A, 5B). In addition, the pooled HMO contained several complex, fucosylated and/or sialylated oligosaccharides. In comparison and as expected, the HPLC-FL profile of GOS looked strikingly different (FIG. 5C) and contained mostly tri- and tetra-saccharides and hardly any complex glycans.

Comparable to published data derived from the same neonatal rat model,[27-29] all DF pups, but only 19 of 26 FF pups (73.1%) survived the first 96 h post-partum (FIG. 6A) (Nadler E P, Dickinson E, Knisely A, et al. J Surg Res 2000; 92:71-7; Upperman J S, Potoka D, Grishin A, et al. Semin Pediatr Surg 2005; 14:159-66; Guner Y S, Franklin A L, Chokshi N K, et al. Lab Invest 2011; 91:1668-79). Most intriguingly, the addition of HMO greatly improved survival (19 of 20 pups, 95.0%). GOS, however, had no effect (13 of 17 pups, 76.5%).

Figures 1, 6:
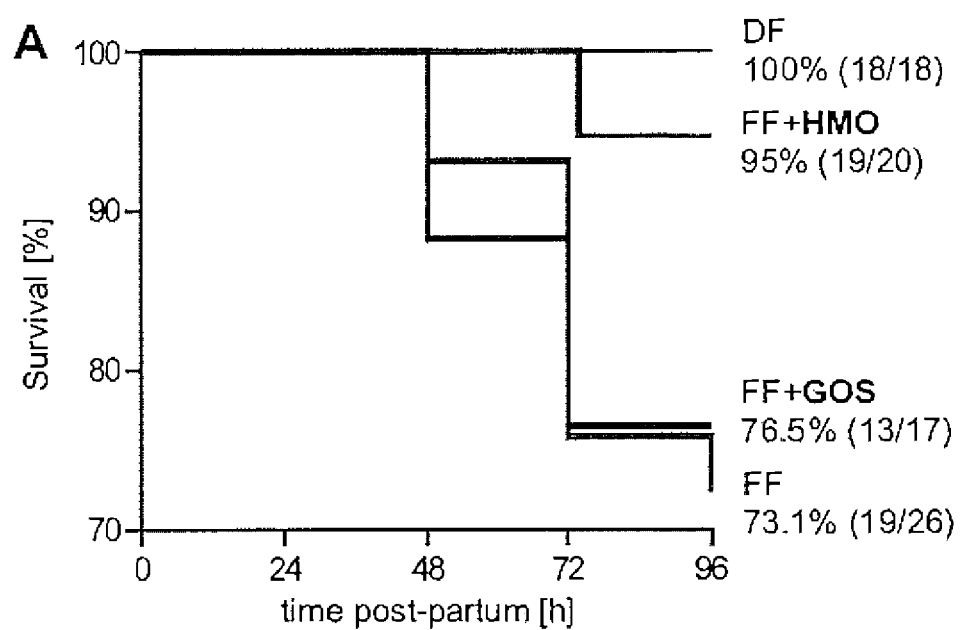
FIG. 6. Pooled human milk oligosaccharides (HMO), but not galacto-oligosaccharides (GOS) improve survival and reduce necrotizing enterocolitis (NEC) in neonatal rats. (A) Survival of neonatal rats within the first 96 h post-partum. DF, dam-fed; FF, formula-fed; FF+HMO, fed formula with HMO (10 mg/ml); FF+GOS, fed formula with GOS (8 mg/ml). (B) Macroscopic evaluation of rat intestines at 96 h post-partum. Compared to DF (left) and FF+HMO (right) animals, the intestines of FF animals (center) were darker with patchy necrosis and evidence of hemorrhagic intestine as well as intramural gas cysts (*Pneumatosis intestinalis*). (C) Microscopic evaluation of H&E-stained rat ileum sections. Based on the presence or absence of histological anomalies (three examples are shown in the bottom panel), ileum sections were graded from 0 (normal) to 4 (complete destruction). (D) Ileum pathology scores at 96 h post-partum. Each intervention was tested in a total of 10-20 animals in three independent experiments. Each symbol represents the pathology score for an individual animal. Horizontal lines represent mean pathology scores. ***$p<0.001$.
Figures 3, 6:
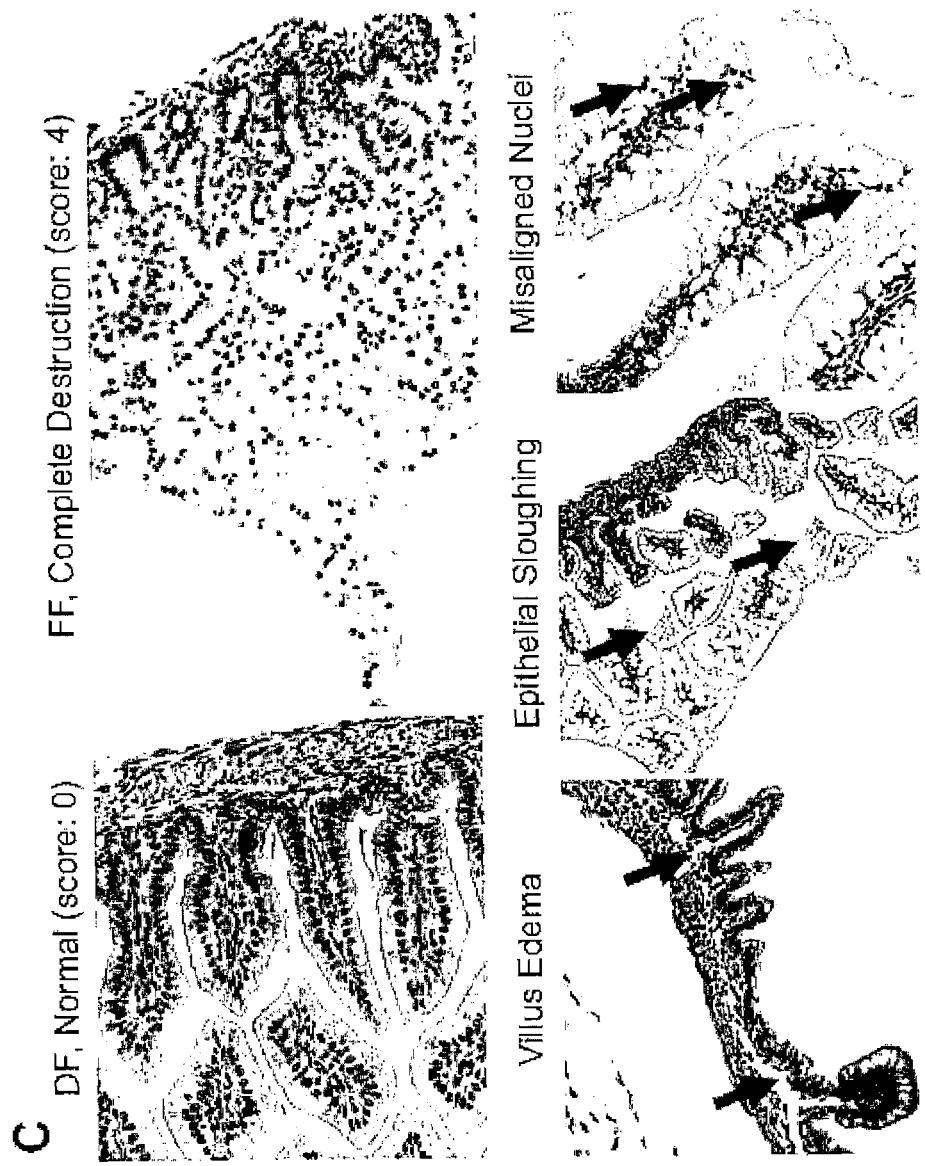
Figures 4, 6:
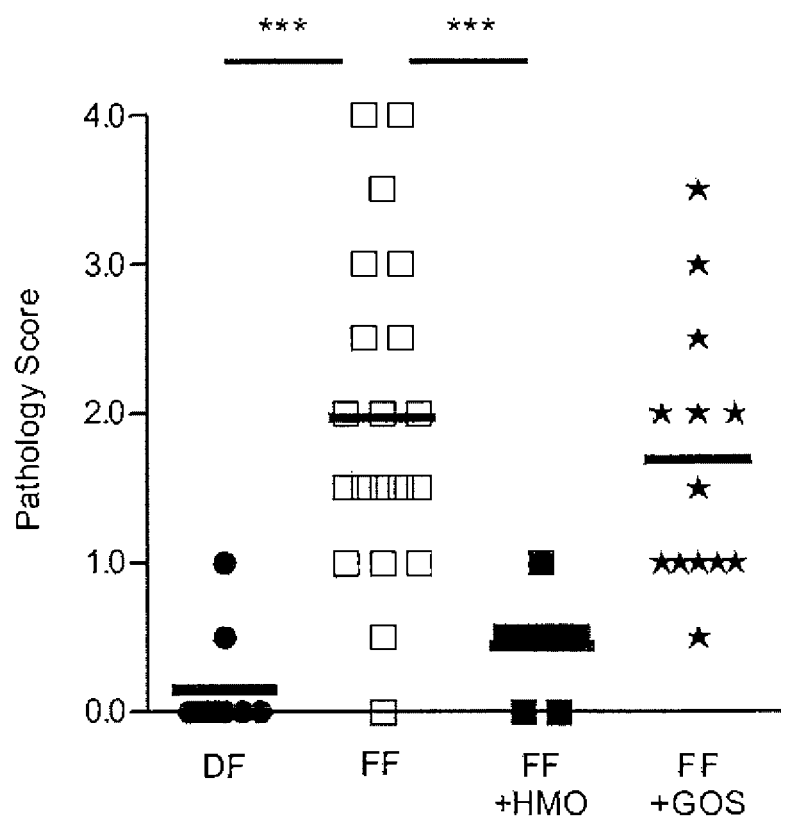

DF pups gained weight faster than FF pups, but the addition of HMO or GOS did not improve weight gain, suggesting that improved survival was independent of weight gain. Macroscopic evaluation 96 h post-partum showed that the intestines of most FF and FF+GOS pups were darker, with patchy necrosis and evidence of hemorrhagic intestine as well as intramural gas cysts (*Pneumatosis intestinalis*), which are characteristic signs of NEC (FIG. 6B) and were absent from the intestines of all DF and most FF+HMO pups. Microscopic evaluation of H&E-stained ileum sections confirmed the macroscopic observations (FIG. 6C). While the ileum of most DF and FF+HMO pups showed a normal, healthy microscopic architecture, some of the sections from FF and FF+GOS pups showed complete destruction. While the mean pathology score (±SD) was 0.15±0.34 in the DF group, it increased significantly to 1.98±1.11 in the FF group ($p<0.001$) (FIG. 6D). Pups that received HMO with their formula (10 mg/ml) had a mean pathology score of 0.44±0.30, which was significantly lower than in the FF group ($p<0.001$), but statistically not different from that of DF pups. Pups that received HMO at a 10-fold lower concentration (1 mg/ml) had a mean pathology score of 0.64±0.54, which was still significantly lower than that in the FF group ($p<0.001$), but slightly higher than in the DF controls ($p<0.05$). GOS had no effect on pathology scores (1.69±0.90). These results demonstrate for the first time that oligosaccharides isolated from human milk improve survival and reduce NEC in a neonatal rat model of the disease.

Figure 7:
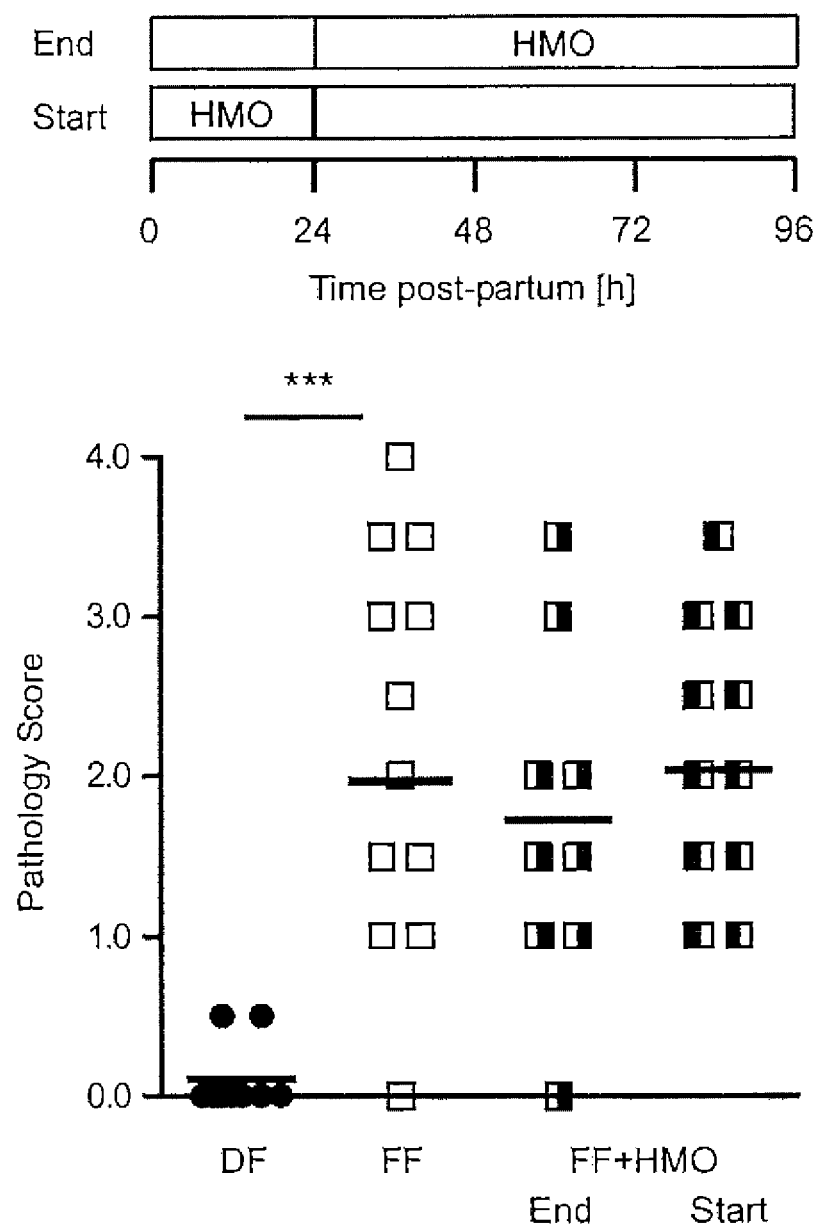
FIG. 7. Exposure to human milk oligosaccharides (HMO) in the first 24 h post-partum is required, but not sufficient to reduce necrotizing enterocolitis. Neonatal rats were dam-fed (DF), fed HMO-free formula for the entire first 96 h post-partum (FF), fed HMO-free formula for the first 24 h and then switched to HMO-containing formula (10 mg/ml) for the remaining 72 h (FF+HMO End), or fed HMO-containing formula for the first 24 h and then switched to HMO-free formula (FF+HMO Start). Each intervention was tested in a total of 9-12 animals in two independent experiments. ***$p<0.001$.

Exposure to HMO in the First 24 h Post-Partum is Required, but not Sufficient to Reduce NEC To assess whether or not HMO have to be present in all feedings to be protective, we fed a group of pups with formula that did not contain HMO for the first 24 h and then switched to formula that was supplemented with HMO for the remaining 72 h (FIG. 7). To our surprise, pathology scores (1.72±1.06) were not different from pups that received unsupplemented formula for the entire duration of the study (1.97±1.15). Another group of pups received formula with HMO for the first 24 h and formula without HMO for the remaining 72 h. Again, pathology scores (2.04±0.80) were not different from the group that received unsupplemented formula for the entire time. Together, these results indicate that exposure to HMO in the first 24 h post-partum is required, but not sufficient to protect from NEC.

A Single, Disialylated HMO Reduces NEC

Figures 1, 8:
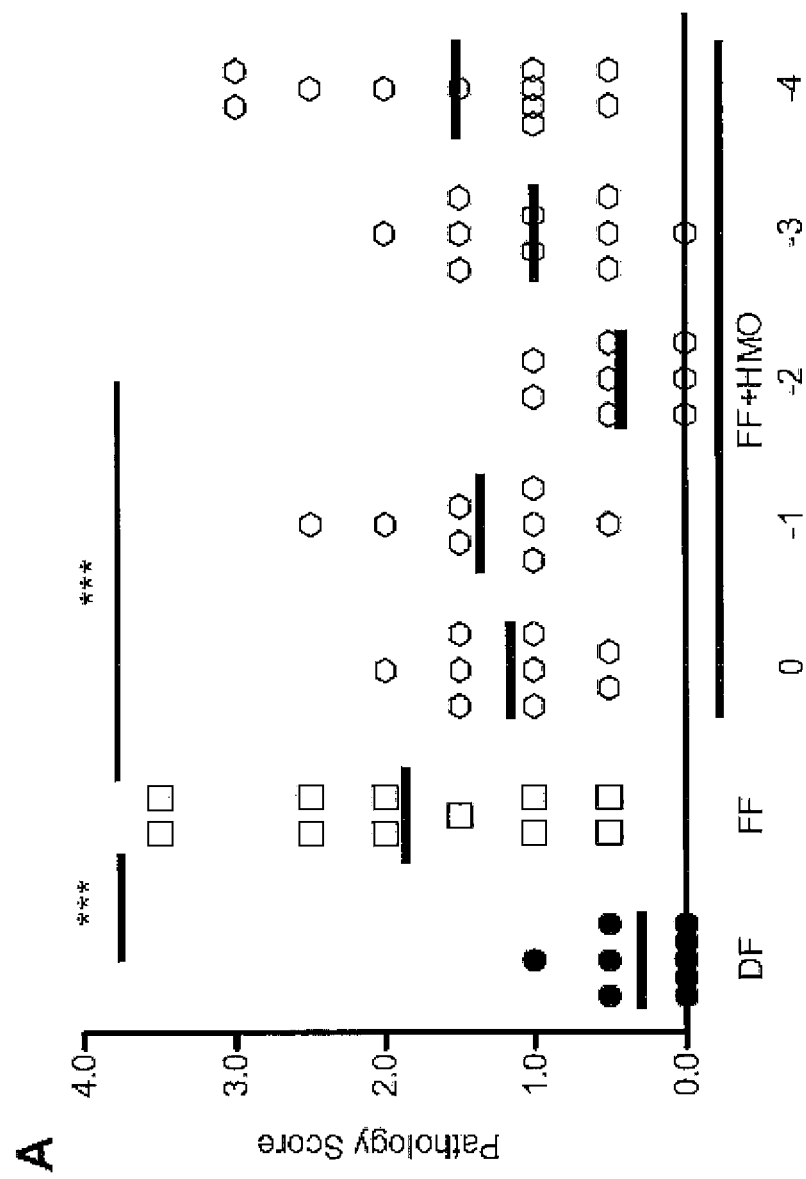
FIG. 8. A single, disialylated human milk oligosaccharide (HMO) reduces necrotizing enterocolitis. (A) Ileum pathology scores in response to adding charge-fractionated HMO to formula. Anion exchange chromatography was used to fractionate pooled HMO by charge based on whether HMO contained no (0), one (−1), two (−2), three (−3) or four (−4) sialic acid residues. The −2 charged HMO fraction, containing oligosaccharides with two sialic acids (two negative charges) had the most pronounced effect, (B) HPLC-FL chromatogram of −2 charged HMO fraction. (C) MALDI-TOF mass spectra and potential composition of the four major HMO peaks in the −2 charged HMO fraction. The predicted number of hexoses (circles), hexosamines (square), N-acetylneuramic acid (NeuAc, diamond) and fucose (triangle) per molecule are listed above each mass spectrum. Loss of NeuAc during analysis reduces the mass by 291 Da. (D) Fast protein liquid chromatography (FPLC) with a gel exclusion column was used to separate the four major HMO peaks in the −2 charged HMO fraction by size. FPLC fractions containing mostly HMO peak 2 were pooled together (HMO 2). HMO peaks 3 and 4 could not be separated by gel exclusion and were pooled in one fraction (HMO 3+4). (E) Ileum pathology scores in response to adding size-fractionated HMO to formula. Each intervention was tested in a total of 11-14 animals in two independent experiments. ***$p<0.001$.
Figures 2, 8:
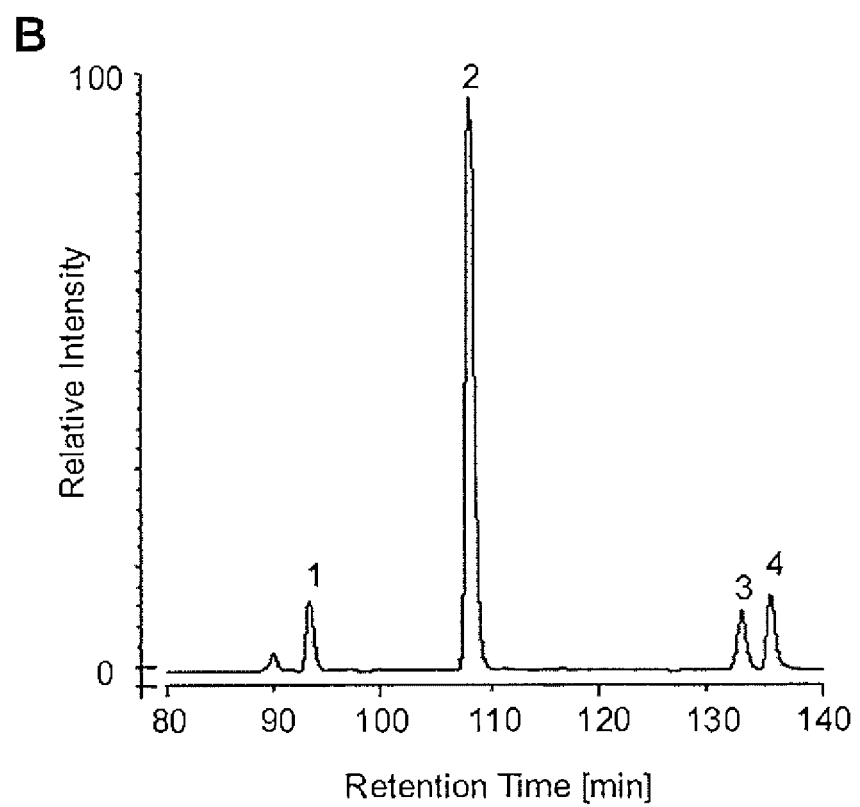
Figures 3, 8:
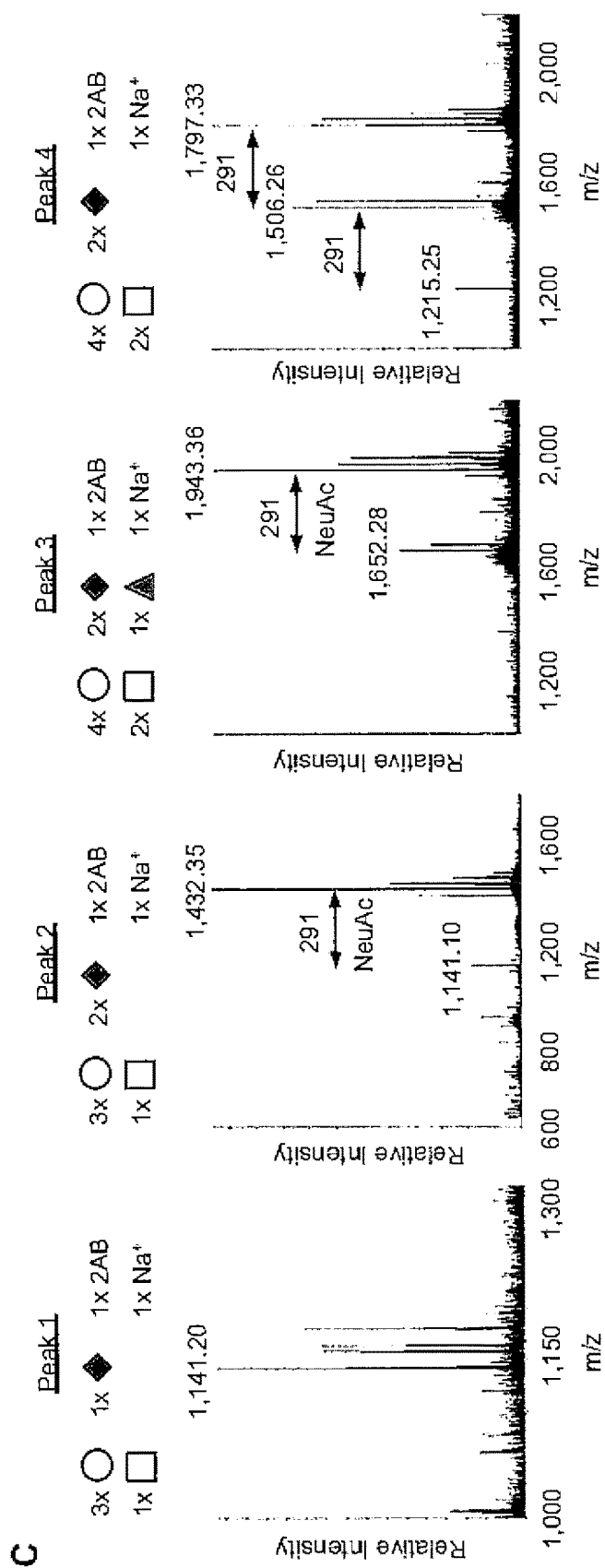
Figures 4, 8:
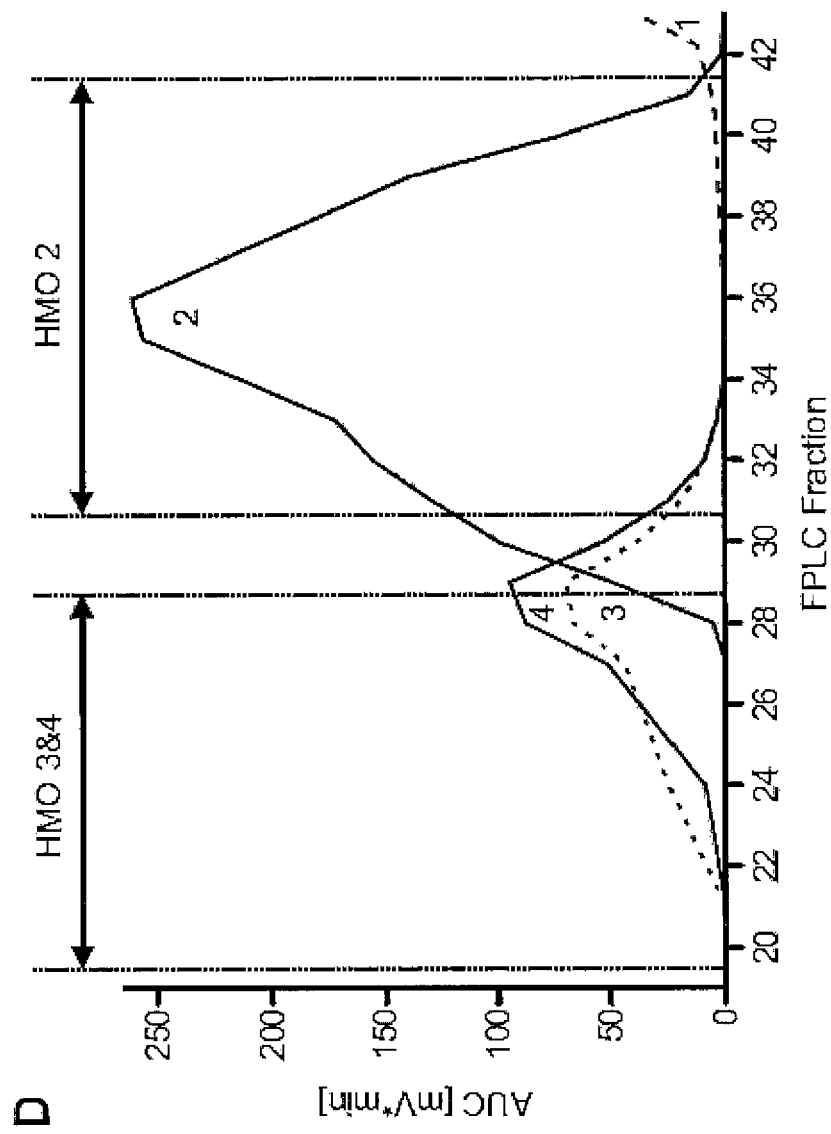
Figures 5, 8:
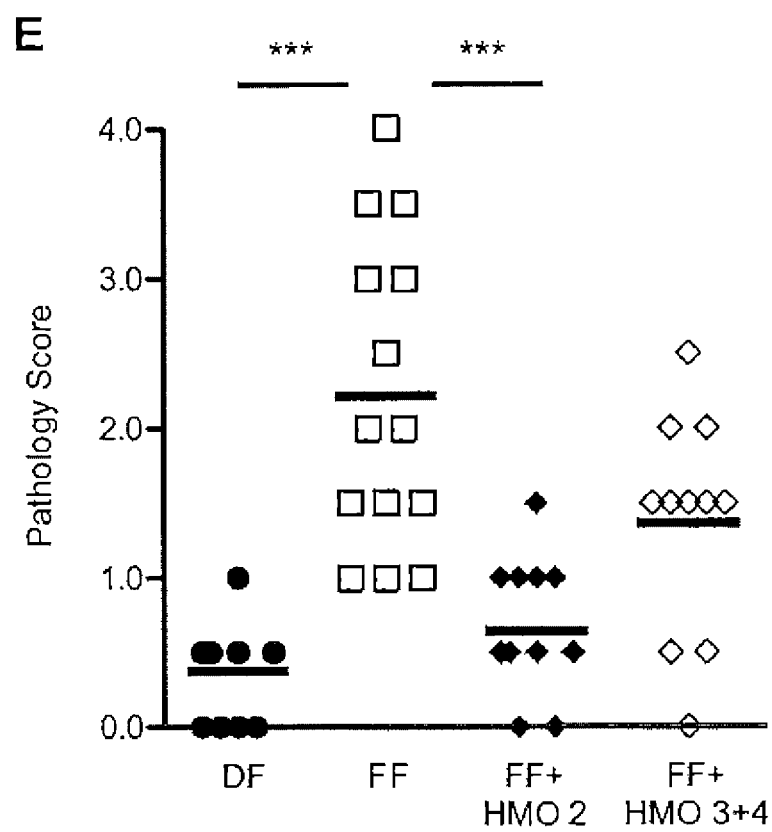

Since more than 150 structurally different HMO have been identified so far, we wondered whether all HMO are protective or whether the effect depends on a specific structural epitope. First, we used anion exchange chromatography to separate the pooled HMO by charge based on the number of sialic acid moieties on the individual HMO. As confirmed by HPLC-FL, we generated five distinct HMO fractions with oligosaccharides that contained either zero, one, two, three or four sialic acids and had a net charge of 0, −1, −2, −3 or −4, respectively. We then tested these fractions in the rat model at their respective concentrations in pooled HMO at 10 mg/ml (FIG. 8A). Adding the neutral (0) HMO fraction to the formula lowered pathology scores to 1.18±0.50 ($p<0.05$). While the −1, −3 and −4 charged HMO fractions had no effect, the −2 charged fraction lowered pathology scores to 0.44±0.42, which was significantly different from the FF group ($p<0.001$), but not different from DF controls. These results showed that not all HMO are protective and that the effects depend on the presence of two sialic acids.

We analyzed the −2 charged HMO fraction by HPLC-FL and detected four distinct peaks (FIG. 8B) which we collected and analyzed by MALDI-TOF-MS (FIG. 8C). The m/z value of peak 1 corresponded to the 2AB-labelled sodium adduct of an oligosaccharide containing three hexoses, one N-acetyl-hexosamine and one N-acetyl-neuraminic acid, likely a monosialylated lacto-N-tetraose (Galβ1-3GlcNAcβ1-3Galβ-4Glc) or lacto-N-neotetraose (Galβ1-4GlcNAcβ1-3Galβ1-4Glc). Since peak 1 contained only one sialic acid and we had shown that the monosialylated (−1) HMO fraction had no significant effect on reducing NEC pathology scores, we assumed that peak 1 was a spillover from the −1 charged HMO fraction and disregarded this oligosaccharide in future analyses. Peak 2 was different from peak 1 only by the addition of one N-acetyl-neuraminic acid and was likely disialylated lacto-N-tetraose or lacto-N-neotetraose. Peaks 3 and 4 contained one additional hexose and one additional N-acetyl-hexosamine, which likely represent an extension of the HMO backbone by the disaccharides N-acetyl-lactosamine (Galβ1-4Glc-NAc) or lacto-N-biose (Galβ1-3GlcNAc). Peak 3 was different from peak 4 only by the addition of a fucose moiety. In the following, the oligosaccharides represented by peaks 2, 3 and 4 are called HMO 2, HMO 3 and HMO 4, respectively.

Next, we used gel exclusion chromatography to further separate the oligosaccharides in the −2 charged HMO fraction by size. While we were unable to separate HMO 3 and 4 from each other, we separated HMO 3+4 from HMO 2 (FIG. 8D). We then pooled the subfractions containing either HMO 2 or HMO 3+4 and tested them in the rat model at their original concentrations in pooled HMO at 10 mg/ml (FIG. 8E). While HMO 3+4 had no effect, HMO 2 reduced pathology scores to 0.64±0.41, which was significantly lower than that of the FF group ($p<0.001$), but not different from DF controls.

The NEC-Protective HMO is DSLNT

Figures 1, 9:
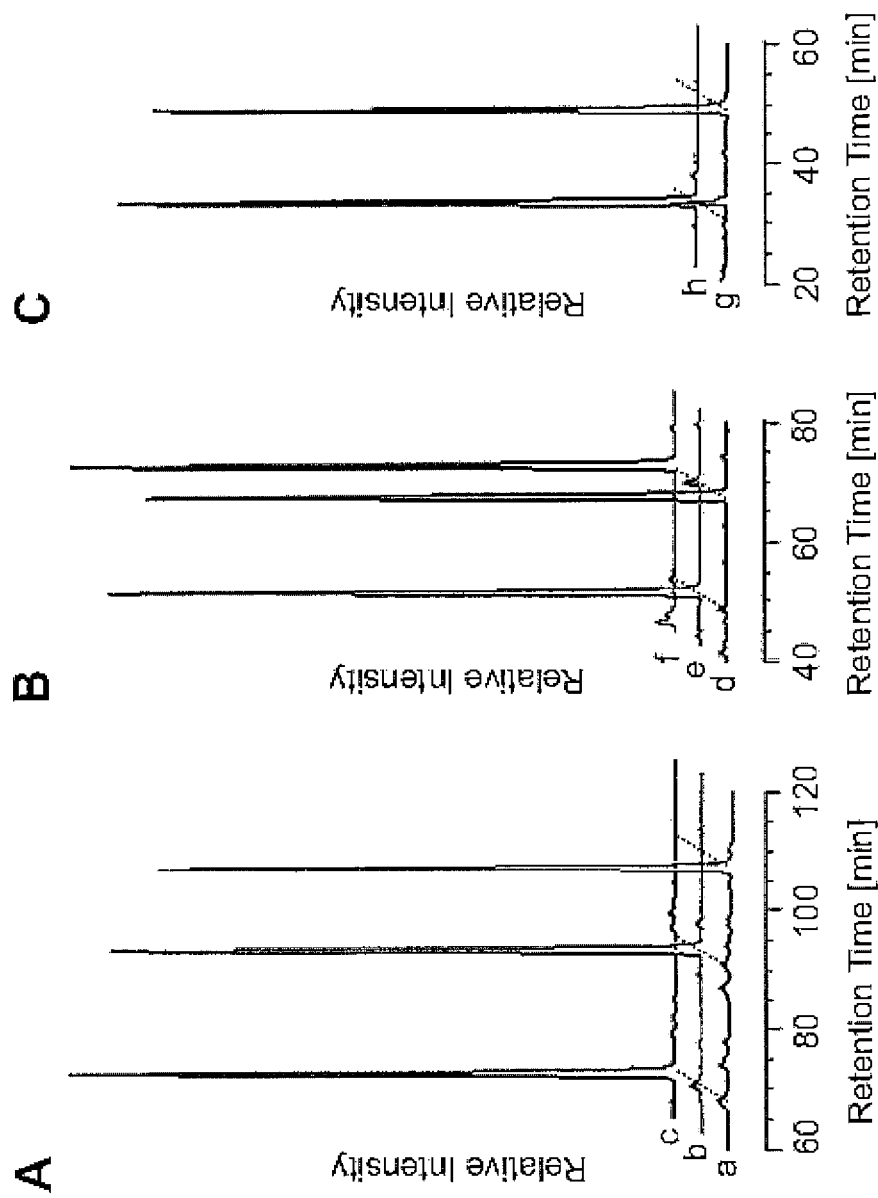
FIG. 9. The necrotizing enterocolitis-protective human milk oligosaccharide (HMO) is disialyllacto-N-tetraose (DSLNT). (A) Linkage specific neuraminidase treatment shows the presence of one α2-3- and one α2-6-linked N-acetyl-neuraminic acid (NeuAc). Fluorescence high-performance liquid chromatography (HPLC-FL) chromatogram a: protective HMO 2; b: HMO 2 after treatment with α2-3-specific neuraminidase; c: HMO 2 after treatment with linkage promiscuous neuramidase. (B) The underlying HMO backbone has a type I structure (Galβ1-3GlcNAc). HPLC-FL chromatogram d: asialo-HMO 2 (after treatment with α2-3/6 neuraminidase, product c); e: asialo-HMO 2 after treatment with β-3-specific galactosidase; f: asialo-HMO 2 after treatment with β1-4-specific galactosidase. (C) The subterminal sugar in the HMO backbone is N-acetylglucosamine (GlcNAc). HPLC-FL chromatogram g: asialo-agalacto-HMO 2 (after treatment with α2-316 neuraminidase and β1-3 galactosidase, product e); h: asialo-agalacto-HMO 2 after treatment with GlcNAcase. (0) Gas chromatography mass spectrum (GC-MS) of partially methylated alditol acetate (PMAA) derivatives of HMO 2. (E) Schematic representation of DSLNT based on the results from sequential exoglycosidase digestion and GC-MS PMAA linkage analysis.
Figures 2, 9:
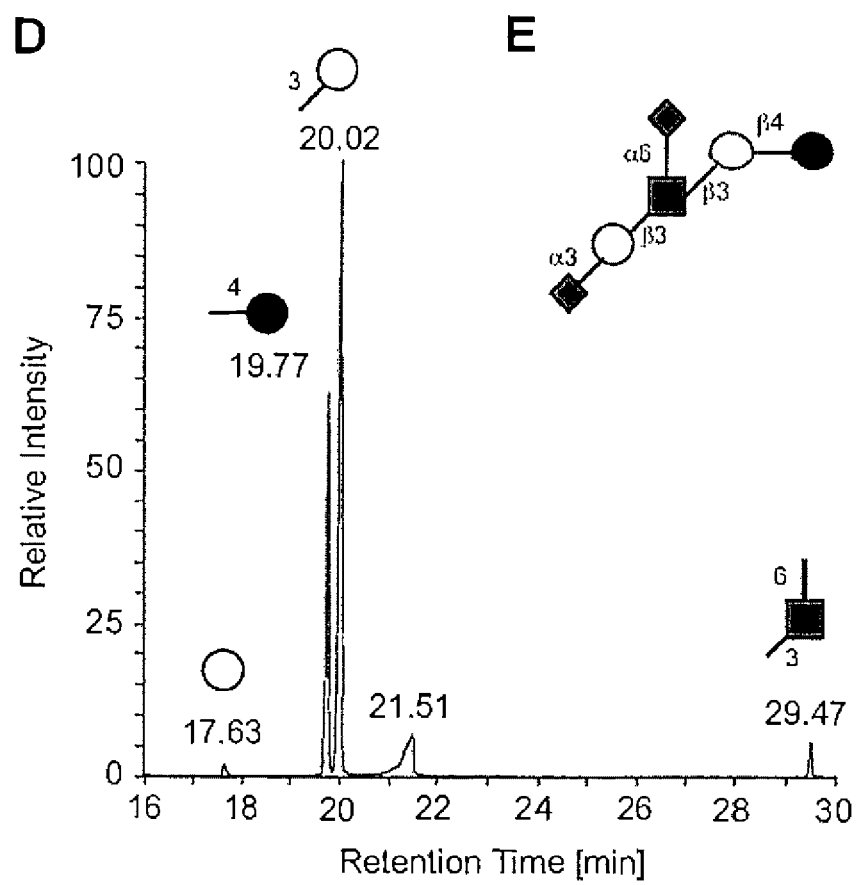

The results of our two-dimensional chromatography approach showed that a distinct disialylated HMO protects neonatal rats from NEC. While MALDI-TOF-MS provided the first insights into the overall composition of the protective HMO, we used HPLC-FL after sequential exoglycosidase digestion to determine the exact positions and linkages of the different monosaccharide residue. First, we determined whether the two sialic acids are bound in an α2-3 or α2-6 linkage. Incubating HMO 2 with an α2-3-specific neuraminidase caused a complete shift of the HMO 2 peak in the HPLC-FL chromatogram (FIG. 9A), indicating that at least one sialic acid is bound in an α2-3 position. Incubating HMO 2 with a linkage promiscuous neuraminidase that cleaves both α2-3- and α2-6-bound sialic acid resulted in an even bigger shift of the HMO 2 peak (FIG. 9A). Together, these results indicate that one sialic acid is bound in an α2-3 linkage and one in an α2-6 linkage. After removal of both sialic acids, we used linkage specific galactosidases to determine whether the terminal monosaccharide is indeed galactose and whether the underlying HMO backbone is a type I (Galβ1-3GlcNAc-R) or type II chain (Galβ1-4Glc-NAc-R). β1-3-specific galactosidase digestion resulted in a complete peak shift; β1-4-specific galactosidase digestion had no effect, confirming the presence of terminal galactose in a type I chain (FIG. 9B). Next, we used a β-N-acetyl-glucosaminidase and confirmed that the subterminal monosaccharide is indeed GlcNAc (FIG. 9C). The remaining disaccharide was cleaved by a β1-4-specific galactosidase, verifying that lactose forms the reducing end of HMO 2.

After elucidating the position and some of the linkages in the HMO backbone, we determined the positions of the two sialic acids. The β1-3-specific galactosidase removed the terminal galactose only after pretreatment with the linkage promiscuous neuraminidase or the α2-3-specific neuraminidase, suggesting that the terminal galactose is capped by α2-3-linked sialic acid. Removal of the subterminal GlcNAc was only possible after pretreatment with the linkage promiscuous but not the α2-3-specific neuraminidase, suggesting that the second sialic acid is bound to the subterminal GlcNAc in α2-6 linkage.

In addition, we used GC-MS analysis of partially methylated alditol acetate (PMAA) derivatives and confirmed the presence of 3-linked galactose, 4-linked glucose and 3,6-linked GlcNAc (FIG. 9D). The combined data of sequential exoglycosidase digestions and PMAA linkage analysis unambiguously identified HMO 2 as DSLNT with the isomeric configuration NeuAcα2-3Galβ1-3 (NeuAcα2-6) GlcNAcβ1-3Galβ1-4Glc (FIG. 9E).

DSLNT has NEC-Protective Effects

Figure 10:
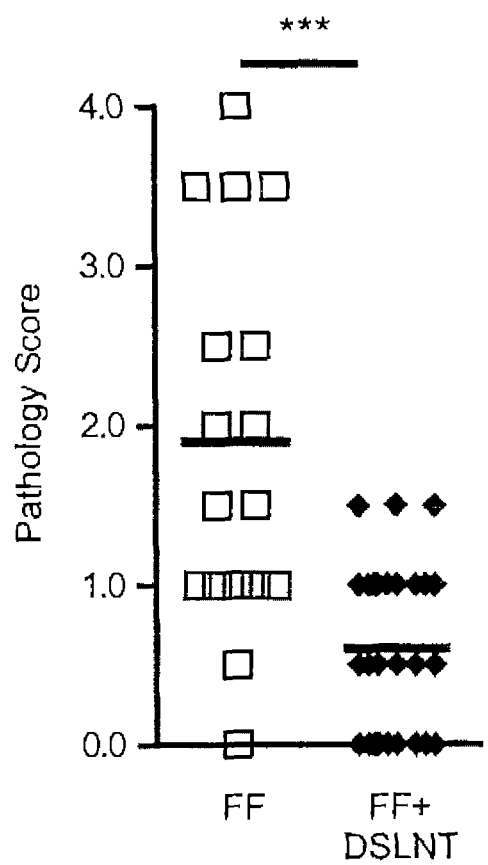
FIG. 10. Commercially available DSLNT shows necrotizing enterocolitis (NEC) protective effects. Ileum pathology scores in response to adding commercially available DSLNT to formula. Commercially available DSLNT (300 μM) significantly reduced NEC pathology scores. Each intervention was tested in a total of 11-26 animals in three independent experiments. ***$p<0.001$.
Figure 10:
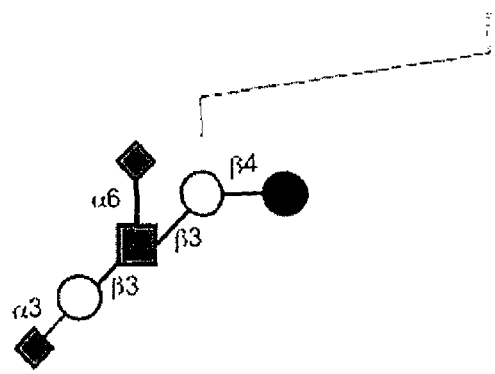

Based on HPLC-FL analysis of the pooled HMO (FIG. 5A), the DSLNT concentration was about 300 μM in formula that we had supplemented with pooled HMO at 10 mg/ml. We purchased commercially available DSLNT, added it to formula at 300 μM, and confirmed that it significantly reduced NEC pathology scores to 0.60±0.52 compared to 1.90±1.13 in the FF group (p<0.001) (FIG. 10).

REFERENCES

1. Uauy R D, Fanaroff A A, Korones S B, et al. Necrotising enterocolitis in very low birth weight infants: biodemographic and clinical correlates. National Institute of Child Health and Human Development Neonatal Research Network. J Pediatr 1991; 119:630-8.
2. Neu J, Walker W A. Necrotizing enterocolitis. N Engl J Med 2011; 364:255-64.
3. Holman R C, Stoll B J, Clarke M J, et al. The epidemiology of necrotizing enterocolitis infant mortality in the United States. Am J Public Health 1997; 87:2026-31.
4. Holman R C, Stoll B J, Curns A T, et al. Necrotising enterocolitis hospitalisations among neonates in the United States. Paediatr Perinat Epidemiol 2006; 20:498-506.
5. Rees C M, Pierro A, Eaton S. Neurodevelopmental outcomes of neonates with medically and surgically treated necrotizing enterocolitis. Arch Dis Child Fetal Neonatal Ed 2007; 92:F193e8.
6. Dicken B J, Sergi C, Rescorla F J, et al. Medical management of motility disorders in patients with intestinal failure: a focus on necrotizing enterocolitis, gastroschisis, and intestinal atresia. J Pediatr Surg 2011; 46:1618-30.
7. Clark, Gordon P, Walker W M, et al. Characteristics of patients who die of necrotizing enterocolitis. J Perinatal. Published Online First: 19 May 2011. doi:10.1038/jp.2011.65.
8. Blakely M L, Lally K P, McDonald S, et al. Postoperative outcomes of extremely low birth-weight infants with necrotizing enterocolitis or isolated intestinal perforation: a prospective cohort study by the NICHD Neonatal Research Network. Ann Surg 2005; 241:984e9; discussion 989-94.
9. Lucas A, Cole T J. Breast milk and neonatal necrotizing enterocolitis. Lancet 1990; 336:1519-23.
10. Sullivan S, Schanler R J, Kim J H, et al. An exclusively human milk-based diet is associated with a lower rate of necrotizing enterocolitis than a diet of human milk and bovine milk-based products. J Pediatr 2010; 15:562-7 e1.
11. Sisk P M, Lovelady C A, Dillard R G, et al. Early human milk feeding is associated with a lower risk of necrotizing enterocolitis in very low birth weight infants. J Perinatol 2007; 27:428-33.
12. Schanler R J, Shulman R J, Lau C. Feeding strategies for premature infants: beneficial outcomes of feeding fortified human milk versus preterm formula. Pediatrics 1999; 103:1150-7.
13. Schanler R J, Lau C, Hurst N M, et al. Randomized trial of donor human milk versus preterm formula as substitutes for mothers' own milk in the feeding of extremely premature infants. Pediatrics 2005; 116:400-6.
14. Newburg D S, Ruiz-Palacios G M, Morrow A L. Human milk glycans protect infants against enteric pathogens. Annu Rev Nutr 2005; 25:37-58.
15. Kunz C, Rudloff S, Barer W, et al. Oligosaccharides in human milk: structural, functional, and metabolic aspects. Annu Rev Nutr 2000; 20:699-722.
16. Bode L. Human milk oligosaccharides: prebiotics and beyond. Nutr Rev 2009; 67 (Suppl 2):S183-91.
17. Bode L. Recent advances on structure, metabolism, and function of human milk oligosaccharides. J Nutr 2006; 136:2127-30.
18. Wu S, Tao N, German J B, et al. Development of an annotated library of neutral human milk oligosaccharides. J Proteome Res 2010; 9:4138-51.
19. Wu S, Grimm R, German J B, et al. Annotation and structural analysis of sialylated human milk oligosaccharides. J Proteome Res 2011; 10:856-68.
20. Stahl B, Thurl S, Zeng J, et al. Oligosaccharides from human milk as revealed by matrix-assisted laser desorption/ionization mass spectrometry. Anal Biochem 1994; 223:218-26.
21. Kobata A. Structures and application of oligosaccharides in human milk. Proc Jpn Acad Ser B Phys Biol Sci 2010; 86:731-47.
22. Thurl S, Henker J, Siegel M, et al. Detection of four human milk groups with respect to Lewis blood group dependent oligosaccharides. Glycoconj J 1997; 14:795-9.
23. Blank D, Gebhardt S, Maass K, et al. High-throughput mass finger printing and Lewis blood group assignment of human milk oligosaccharides. Anal Bioanal Chem 2011; 401:2495-510.
24. Bode L, Kunz C, Muhly-Reinholz M, et al. Inhibition of monocyte, lymphocyte, and neutrophil adhesion to endothelial cells by human milk oligosaccharides. Thromb Haemost 2004; 92:1402-10.
25. Bode L, Rudloff S, Kunz C, et al. Human milk oligosaccharides reduce plateletneutrophil complex formation leading to a decrease in neutrophil beta 2 integrin expression. J Leukoc Biol 2004; 76:820-6.
26. Barlow B, Santulli T V. Importance of multiple episodes of hypoxia or cold stress on the development of enterocolitis in an animal model. Surgery 1975; 77:687-90.
27. Nadler E P, Dickinson E, Knisely A, et al. Expression of inducible nitric oxide synthase and interleukin-12 in experimental necrotizing enterocolitis. J Surg Res 2000; 92:71-7.
28. Upperman J S, Potoka D, Grishin A, et al. Mechanisms of nitric oxide-mediated intestinal barrier failure in necrotizing enterocolitis. Semin Pediatr Surg 2005; 14:159-66.
29. Guner Y S, Franklin A L, Chokshi N K, et al. P-glycoprotein induction by breast milk attenuates intestinal inflammation in experimental necrotizing enterocolitis. Lab Invest 2011; 91:1668-79.
30. Stefanutti G, Lister P, Smith V V, et al. P-selectin expression, neutrophil infiltration, and histologic injury in neonates with necrotizing enterocolitis. J Pediatr Surg 2005; 40:942-7; discussion 947-8.
31. Becker D J, Lowe J B. Leukocyte adhesion deficiency type II. Biochim Biophys Acta 1999; 1455:193-204.
32. Luhn K, Wild M K, Eckhardt M, et al. The gene defective in leukocyte adhesion deficiency II encodes a putative GDP-fucose transporter. Nat Genet 2001; 28:69-72.
33. Crocker P R, Paulson J C, Varki A. Siglecs and their roles in the immune system. Nat Rev Immunol 2007; 7:255-66.

34. Koliwer-Brandl H, Siegert N, Umnus K, et al. Lectin inhibition assay for the analysis of bioactive milk sialoglycoconjugates. Int Dairy J 2011; 21:413-20.
35. Sodhi C, Richardson W, Gribar S, et al. The development of animal models for the study of necrotizing enterocolitis. Dis Model Mech 2008; 1:94-8.
36. Ganapathy V, Hay J W, Kim J H. Costs of necrotizing enterocolitis and cost-effectiveness of exclusively human milk-based products in feeding extremely premature infants. Breastfeed Med. Published Online First: 30 Jun. 2011. doi:10.1089/bfm.2011.0002.
37. Leo F, Asakuma 5, Fukuda K, et al. Determination of sialyl and neutral oligosaccharide levels in transition and mature milks of Samoan women, using anthranilic derivatization followed by reverse phase high performance liquid chromatography. Biosci Biotechnol Biochem 2010; 74:298-303.
38. Bao Y, Zhu L, Newburg D S. Simultaneous quantification of sialyloligosaccharides from human milk by capillary electrophoresis. Anal Biochem 2007; 370:206-14.

What is claimed is:

1. An infant formula or baby food comprising a formulation that is substantially free of non-disialyllacto-N-tetraose (DSLNT) oligosaccharides, which comprises a pharmaceutically acceptable carrier and an isolated compound selected from the group consisting of α-Neu5Ac-(2→3)-α-Gal-(1→3)-[α-Neu5Ac-(2→6)]-β-GlcNAc-(1→3)-β-Gal-(1→4)-Glc, α-Neu5Ac-(2→3)-β-Gal-(1→3)-[α-Neu5Ac-(2→6)]-α-GlcNAc-(1→3)-β-Gal-(1→4)-Glc, α-Neu5Ac-(2→3)-β-Gal-(1→3)-[α-Neu5Ac-(2→6)]-β-GlcNAc-(1→3)-β-Gal-(1→4)-Glc, β-Neu5Ac-(2→3)-β-Gal-(1→3)-[α-Neu5Ac-(2→6)]-β-GlcNAc-(1→3)-β-Gal-(1→4)-Glc, and α-Neu5Ac-(2→3)-β-Gal-(1→3)-[β-Neu5Ac-(2→6)]-β-GlcNAc-(1→3)-β-Gal-(1→4)-Glc, wherein the formulation comprises at least 800 μM or greater of the compound.

2. The infant formula or baby food of claim 1, which is a liquid, a gel, or a solid.

3. The infant formula or baby food of claim 1, wherein the formulation additionally comprises a probiotic.

4. The infant formula or baby food of claim 3, wherein the probiotic comprises bacterial species from the genera *Bifidobacteria* and/or *Lactobacilli*.

5. The infant formula of claim 1 further comprising a vitamin and/or mineral.

* * * * *